US 7,228,170 B2

(12) United States Patent
Zhu et al.

(10) Patent No.: US 7,228,170 B2
(45) Date of Patent: *Jun. 5, 2007

(54) DEVICE AND METHOD FOR MONITORING AND CONTROLLING PHYSIOLOGIC PARAMETERS OF A DIALYSIS PATIENT USING SEGMENTAL BIOIMPEDANCE

(75) Inventors: Fansan Zhu, Flushing, NY (US); Nathan W. Levin, New York, NY (US)

(73) Assignee: Renal Research Institute, LLC, New York, NY (US)

( * ) Notice: Subject to any disclaimer, the term of this patent is extended or adjusted under 35 U.S.C. 154(b) by 64 days.

This patent is subject to a terminal disclaimer.

(21) Appl. No.: 10/305,513

(22) Filed: Nov. 27, 2002

(65) Prior Publication Data

US 2003/0120170 A1    Jun. 26, 2003

Related U.S. Application Data

(63) Continuation-in-part of application No. 09/638,657, filed on Aug. 14, 2000, now Pat. No. 6,615,077.

(51) Int. Cl.
*A61B 5/05* (2006.01)

(52) U.S. Cl. ..................................... 600/547
(58) Field of Classification Search ................ 600/547, 600/483, 322, 300, 310, 323–327, 504–506, 600/531–538, 485, 529, 490, 500; 604/66, 604/67; 210/646, 647
See application file for complete search history.

(56) References Cited

U.S. PATENT DOCUMENTS

| 4,008,712 | A | 2/1977 | Nyboer et al. |
|---|---|---|---|
| 4,016,868 | A | 4/1977 | Allison et al. |
| 4,204,545 | A | 5/1980 | Yamakoshi |
| 4,370,983 | A | 2/1983 | Lichtenstein |
| 5,063,937 | A | 11/1991 | Ezenwa et al. |
| 5,449,000 | A | 9/1995 | Libke et al. |
| 5,580,460 | A | 12/1996 | Polaschegg |
| 5,735,284 | A | 4/1998 | Tsoglin et al. |
| 5,778,643 | A | 7/1998 | Tacchini |
| 6,228,033 | B1 | 5/2001 | Köö bi et al. |
| 6,246,894 | B1 | 6/2001 | Steuer et al. |
| 6,615,077 | B1 * | 9/2003 | Zhu et al. ................... 600/547 |
| 6,733,676 | B2 | 5/2004 | Takai |
| 2004/0092841 | A1 | 5/2004 | Singer |

FOREIGN PATENT DOCUMENTS

| EP | 1 205 144 | 5/2002 |
|---|---|---|
| GB | 2 069 706 | 8/1981 |
| WO | WO 92/19153 | 11/1992 |
| WO | WO 96/32883 | 10/1996 |
| WO | WO 98 51211 | 11/1998 |
| WO | WO 02/13691 | 2/2002 |

OTHER PUBLICATIONS

Zhu et al., "Validating of Changes in Extracellular Volume Measured During Hemodialysis Using a Segmental Bioimpednace Technique", ASAIO Journal, 1998, pp. M541-545.

(Continued)

*Primary Examiner*—Max Hindenburg
*Assistant Examiner*—Brian Szmal
(74) *Attorney, Agent, or Firm*—Kenyon & Kenyon LLP

(57) ABSTRACT

The present invention includes a method of determining the dry body weight of a patient undergoing dialysis by means of segmental bioimpedance analysis. In preferred embodiments, dry body weight is determined by comparison to the bioimpedance values of normal subjects or by monitoring changes in bioimpedance during dialysis. One embodiment of the present invention is a device for determining dry body weight during dialysis.

10 Claims, 12 Drawing Sheets

OTHER PUBLICATIONS

P.M. Kouw et al. "Assessment of post-dialysis dry weight: An application of the conductivity measurment method," Kidney Int., vol. 41 (1992), pp. 440-444.

Piccoli A. "Identification of operational clues to dry weight prescription in hemodialysis using bioimpedance vector analysis," Kidney Int., vol. 53 (1998), pp. 1036-1043.

J.P. de Vries et al. "Non-invasive monitoring of blood volume during hemodialysis: Its relation with post-dialytic dry weight," Kidney Int. vol. 44 (1993), pp. 851-854.

J.K. Leypoldt et al. "Determination of circulating blood volume by continuously monitoring hematocrit during hemodialysis," Journal Am. Soc. Nephrol. vol 6 (1995), pp. 214-219.

J.K. Leypoldt et al. "Evaluating volume status in hemodialysis patients," Adv. Ren. Replace. Ther., vol. 5 (1998), pp. 64-74.

J.G. Webster. "Measurement of Flow and Volume of Blood," *Medicinal Instrumentation Application and Design*, Wiley, New York, 3rd Ed. (1998) pp. 357-362.

Zhu et al., "Estimation of volume of fluid in the peritoneal cavity by bioimpedance analysis", BMES/EMBS Conference, 1999, Proceedings of the First Joint Atlanta, GA, USA 13-16 Oct. 1999.

Shimazu et al., "Electric Impedance Cuff For the Indirect Measurement of Blood Pressure and Volume Elastic Modulus in Human Limb and Finger Arteries", Medical and Biological Engineering and Computing, Peter Peregrinus Ltd., Stevenage, GB. vol. 27, No. 5, Sep. 1, 1989, pp. 477-483.

Zhu et al., "Determination of dry weight in hemodialysis patients by monitoring changes in the slope of extracellular volume (ECV) during dialysis", ASAIO Renal Abstracts, Jun. 2002, p. 180.

an Abstract entitiled "Estimation of Dry Weight in Hemodialysis Patients by Continuous Segmental Bioimpedance Analysis (SBIA)," Zhu et al., submitted in May 2002 to the American Society of Nephrology (ASN) 35th Annual Meeting & Scientific Exposition Submission Program, and presented at the ASN 35th Annual Meeting & Scientific Exposition Submission Program which was conducted on Nov. 1-4, 2002.

slides entitled "Estimation of Dry Weight in Hemodialysis Patients by Continuous Segmental Bioimpedance Analysis," Zhu et al., which were presented, along with the aforementioned Abstract of the same title, at the ASN 35th Annual Meeting & Scientific Exposition Submission Program which was conducted on Nov. 1-4, 2002.

Kubicek et al,. "Development and Evaluation of an Impedance Cardiac Output System", Aerospace Medicine, Aerospace Medical Association, Washington DC, 37(12)1208-1212, 1966.

Patent Absracts of Japan, vol. 1998, No. 8, 1998, (JP 10071130)Figures 1 and 2.

Zhu et al., "Validation of Changes in Extracellular Volume Measured During Hemodialysis Using a Segmental Bioimpedance Technique", ASAIO Journal, 1998, M541-M545.

* cited by examiner

DEVICE AND METHOD FOR MONITORING AND CONTROLLING PHYSIOLOGIC PARAMETERS OF A DIALYSIS PATIENT USING SEGMENTAL BIOIMPEDANCE

CROSS-REFERENCE TO RELATED APPLICATIONS

This application is a continuation-in-part of prior U.S. patent application Ser. No. 09/638,657, filed Aug. 14, 2000 now U.S. Pat. No. 6,615,077, the contents of which are incorporated herein by reference.

FIELD OF THE INVENTION

The present invention relates to a device and method that utilize segmental bioimpedance for monitoring and controlling physiologic parameters of a dialysis patient.

BACKGROUND OF THE INVENTION

Accurate assessment of a dialysis patient's hydration status and prediction of dry body weight (DW or dry weight) is a major problem in the clinical management of the dialysis patient. In both hemodialysis and peritoneal dialysis patients, dry weight is the target weight at the end of dialysis treatment which best reflects removal of excess water from the body. In clinical practice, estimation of DW is an imprecise undertaking, and depends to a large extent on the treating physician's interpretation, based on his or her medical experience and familiarity with the particular patient's condition, of clinical symptoms and signs such as changes in the blood pressure, pulse, and weight of the patient. The correct interpretation of such signs and symptoms is complicated by the fact that the pre-treatment body weight varies for each treatment, the amount of excess fluid is not constant and the amount of fluid that can or should be removed from any particular patient during any particular dialysis treatment may be limited by an individual's cardiovascular tolerance, often manifested by clinical signs and symptoms, such as pretibial edema, dyspnea, cramps and/or a decline in blood pressure. Alternatively, an overestimation of the amount of fluid to be removed may result in potentially avoidable symptoms, unnecessarily lengthy dialysis treatments and often prolonged stays at the dialysis facility. Therefore, over- or underestimation of DW will significantly affect both the efficiency of dialysis treatment and patients' quality of life.

Bioelectrical impedance analysis (BIA) has been recognized as a noninvasive and simple technique to measure body hydration and hydration status (i.e. over-, under- or normal hydration) of subjects for more than twenty years. There is substantial literature on using BIA for the study of dry weight. Kouw et al proposed a method to measure changes in regional conductivity, and then to measure regional extracellular volume (ECV) and intracellular volume (ICV) by BIA. See, P. M. Kouw, et al, *Assessment of post-dialysis dry weight: an application of the conductivity measurement method*. Kidney Int. 41:440–444,1992. However, Kouw's method cannot be used to measure interstitial fluid alone as it does not distinguish between interstitial fluid and plasma, both of which make up the ECV compartment. Piccoli published a method of BIA vector analysis which uses the ratio of resistance to reactance to identify dry weight. While this technique could be used to compare the subjects' body hydration, it is unable to predict individual patient's dry weight because of the significant variation in measured values. See, Piccoli A: *Identification of operational clues to dry weight prescription in hemodialysis using bioimpedance vector analysis*. Kidney Int. 5 3:1036–1043, 1998

Recently, there have been increased numbers of dry weight studies using blood volume (BV) measurements. See, for example, J. P. de Vries et al, *Non-invasive monitoring of blood volume during hemodialysis: Its relation with post-dialytic dry weight*. Kidney Int 44:851–854,1993, and J. K. Leypold, et al, *Determination of circulating blood volume by continuously monitoring hematocrit during hemodialysis*. J. Am. Soc. Nephrol. 6:214–219,1995. Blood volume measurement is a noninvasive technique that can be used to indicate water concentration in blood, i.e. hematocrit, during hemodialysis, but it cannot be used to directly determine dry weight because changes in blood volume are mainly dependent on the rate of vascular refilling which, in part, is independent of body hydration. See, e.g., J. K. Leypoldt, et al, *Evaluating volume status in hemodialysis patients*. Adv. Ren. Replace. Ther. 5:64–74,1998. On the other hand, since a change in the hematocrit level may alter conductivity in the blood during dialysis, it is difficult to obtain information about tissue hydration by either traditional bioelectrical impedance analysis or blood volume analysis. To date, a major problem has been how to measure resistivity of blood and tissue separately, in order to estimate the fluid volume in the intravascular compartment and the interstitial compartment, respectively.

Thus, there is a need for a precise, easily used and operator independent method for determining the hydration status of a dialysis patient, identifying or predicting the dry weight of such a patient and calculating the amount of fluid that should be removed during a dialysis session. In addition, there is a need for a method of controlling dialysis in response to a patient's hydration status.

SUMMARY OF THE INVENTION

The present invention includes a method for determining the hydration status of a dialysis patient comprising the steps of measuring the resistivity of a body segment of the patient, correlating the measured resistivity with predetermined normal dry weight values, and deriving the patient's hydration status. Optionally the resistivity of the interstitial fluid in the body segment is measured to derive the patient's hydration status. In one embodiment, the resistivity of the body segment is determined while applying a pressure of at least about systolic blood pressure, optionally from about 120 mmHg to about 240 mmHg. The body segment can be a limb segment, preferably a calf segment.

Included, is a method for determining a hemodialysis patient's dry weight comprising the steps of periodically measuring the resistivity of a body segment during hemodialysis; comparing successive resistivity measurements; and identifying the patient's dry weight when a substantially constant resistivity is reached. Optionally, resistivity is measured from about every 5 minutes to about every 20 minutes during hemodialysis, preferably about every 10 minutes during hemodialysis. In one embodiment the resistivity of the body segment is measured at a pressure of at least about systolic blood pressure, optionally from about 120 mmHg to about 240 mmHg.

The present invention includes a method for dialysing a patient to the patient's dry weight that comprises measuring the resistivity of a body segment of the patient, correlating the measured resistivity with predetermined normal dry weight values, deriving the patient's hydration, and continuing hemodialysis until the resistivity of the body segment correlates with the predetermined normal dry weight values, preferably measuring the resistivity of the body segment at a pressure of at least about systolic blood pressure.

Also provided is a method for hemodialysing a patient to the patient's dry weight comprising the steps of periodically measuring the resistivity of a body segment during hemodialysis, comparing successive resistivity measurements, and discontinuing hemodialysis when a substantially constant resistivity is reflected. Preferably, the resistivity of the body segment is measured at a pressure of at least about systolic blood pressure. In this embodiment, the resistivity of the body segment is measured from about every 5 minutes to about every 20 minutes during hemodialysis.

The present invention also provides a method of monitoring the heart rate of a hemodialysis patient comprising the steps of determining a time interval between two successive bioimpedance wave peaks and multiplying the reciprocal of the time interval by 60 to obtain the heart rate, and a method of calculating the cardiac output of a patient in need thereof comprising the steps of measuring the stroke volume in an arm segment by bioimpedance analysis, substantially simultaneously measuring the stroke volume in an ipsalateral leg segment by bioimpedance analysis, summing the stroke volume in the arm segment and the stroke volume in the leg segment, and multiplying the sum by twice the heart rate to obtain the cardiac output. Preferably, the stroke volume of the arm segment is calculated by applying an external maximum pressure to the arm segment and determining the change in blood volume in the arm segment between the point of maximum pressure and the point at which no external pressure is applied divided by the number of heart beats between the two points in time, and the stroke volume of the leg is calculated by applying an external maximum pressure to the leg segment and determining the change in blood volume in the leg segment between the point of maximum pressure and the point at which no external pressure is applied divided by the number of heart beats between two points in time.

Included is a device for controlling a hemodialysis machine comprising a bioimpedance analysis measurement unit in electrical communication with a hemodialysis machine, an electrical output means that is in electrical communication with the bioimpedance analysis measurement unit and that is attachable to a body segment, the electrical output means is adapted to apply electrical current to the body segment, an electrical input means that is in electrical communication with the bioimpedance analysis measurement unit and is attachable to a body segment, the electrical input means being adapted to receive the current transmitted through the body segment and transmit the same to the bioimpedance analysis measurement unit. The bioimpedance analysis measurement unit is adapted to determine body segment resistivity based on the current transmitted through the body segment and the bioimpedance analysis measurement unit provides feedback to the hemodialysis machine in response to the body segment resistivity. In one preferred embodiment, the device includes means for applying pressure to the body segment, the pressure applying means is in electrical communication with the bioimpedance analysis measurement unit. Optionally, the pressure applying means includes a pressure cuff that is adapted to encircle the body segment. Preferably, the electrical output means includes at least two injector electrodes, the electrical input means includes at least two measurement electrodes. The injector electrodes and the measurement electrodes are secured to the pressure cuff. Optionally, the pressure cuff includes at least one conductive band with opposing ends and a conductive plate positioned adjacent one of the ends of the conductive band, the conductive band extends substantially the length of the pressure cuff. The conductive plate is arranged to electrically contact the conductive band at a point along the length of the same wherein the distance between the conductive plate and the point of contact of the conductive band is substantially equal to the circumference of the body segment, and wherein the bioimpedance analysis measurement unit is adapted to electrically determine body segment circumference based on the distance between the end of the band adjacent to the plate and the point of contact of the plate along the length of the band.

One embodiment is a device for monitoring hydration status in a hemodialysis patient comprising a bioimpedance analysis measurement unit, an electrical output means, optionally comprising at least two injector electrodes, being in electrical communication with the bioimpedance analysis measurement unit and being attachable to a body segment, the electrical output means being adapted to apply electrical current to the body segment, an electrical input means, optionally comprising at least two measurement electrodes, being in electrical communication with the bioimpedance analysis measurement unit and being attachable to a body segment, the electrical input means being adapted to receive the current transmitted through the body segment and transmit the same to the bioimpedance analysis measurement unit. The bioimpedance analysis measurement unit is adapted to determine body segment resistivity based on the current transmitted through the body segment. Optionally the device includes a hemodialysis machine. Optionally the device includes means for applying pressure to the body segment, optionally a pressure cuff. The pressure applying means being in electrical communication with the bioimpedance analysis measurement unit.

One embodiment of the device includes a pressure cuff with at least one conductive band with opposing ends and a conductive plate positioned adjacent one of the ends of the conductive band. The conductive band extends substantially the length of the pressure cuff and is arranged to electrically contact the conductive band at a point along the length of the same wherein the distance between the conductive plate and the point of contact of the conductive band is substantially equal to the circumference of the body segment, and wherein the bioimpedance measurement unit is adapted to electrically determine body segment circumference based on the distance between the end of the band adjacent to the plate and the point of contact of the plate along the length of the band.

The present invention includes a device for calculating cardiac output through bioimpedance measurements of a patient comprising a bioimpedance measurement unit, a first electrical output means being in electrical communication with the bioimpedance analysis measurement unit and being attachable to an arm segment, the first electrical output means being adapted to apply electrical current to the arm segment, a second electrical output means being in electrical communication with the bioimpedance analysis measurement unit and being attachable to a leg segment, the second electrical output means being adapted to apply electrical current to the leg segment, a first electrical input means being in electrical communication with the bioimpedance analysis measurement unit and being attachable to an arm segment, the electrical input means being adapted to receive the current transmitted through the arm segment and transmit the same to the bioimpedance analysis measurement unit, a second electrical input means being in electrical communication with the bioimpedance analysis measurement unit and being attachable to a leg segment, the electrical input means being adapted to receive the current transmitted through the leg segment and transmit the same to the bioimpedance analysis measurement unit, a first pressure applying means for applying a maximum pressure to the arm segment, the first pressure applying means being in electrical communication with the bioimpedance analysis measurement unit, a second pressure applying means for applying a maximum pressure to the arm segment, the second pressure applying means being in electrical communication with the bioimpedance analysis measurement unit, means for selectively electronically connecting the bioimpedance analysis measurement between the first electrical input and output mans and the second electrical input and output means, and wherein the bioimpedance analysis measurement unit is adapted to selectively measure stroke volume in the arm and leg segments by bioimpedance analysis.

Another embodiment of the present invention includes a device for monitoring the hydration status in, or determining the dry weight of, a hemodialysis patient. The device comprises a digital signal processor, an electrical output means, optionally comprising at least two injector electrodes, being in electrical communication with the digital signal processor and being attachable to a body segment, the electrical output means being adapted to apply electrical current to the body segment, an electrical input means, optionally comprising at least two measurement electrodes, being in electrical communication with the digital signal processor and being attachable to a body segment, the electrical input means being adapted to receive the current transmitted through the body segment and transmit the same to the digital signal processor, and a microprocessor being in electrical communication with the digital signal processor. The microprocessor is adapted to determine a relative change in extracellular volume in the body segment based on the current transmitted through the body segment, and to plot said relative change as a function of time. The digital signal processor is adapted to determine body segment resistivity based on the current transmitted through the body segment. Optionally, the device includes other elements, such as, for example, a hemodialysis machine, a display, an A/D converter, and a D/A converter. The electrical connections and/or electrical communications referenced herein may be accomplished by a number of means readily apparent to one of ordinary skill in the art, but preferably by electrical cables.

Other objects, features and advantages of the invention will be readily apparent from the following detailed description of a preferred embodiment thereof taken in conjunction with the drawings.

BRIEF DESCRIPTION OF THE FIGURES

FIG. 1A represents the situation in which no external pressure is applied to the segment and the blood vessels are uncompressed. FIG. 1B illustrates the situation in which external pressure is applied to the segment and the blood vessels are compressed.

DETAILED DESCRIPTION OF THE INVENTION

The present invention provides a method of determining hemodialysis and peritoneal dialysis patients' hydration status, or more specifically, dry weight, to facilitate the appropriate dialysis prescription. The invention comprises a means of determining and monitoring the resistivity of the patient's body or body segment, and hence the correct dry weight or desired hydration status of a patient undergoing dialysis. The invention further provides a method for determining and monitoring various physiologic parameters of the patient undergoing dialysis, including but not limited to heart rate (HR) and cardiac output (CO).

From a physiological point of view, in healthy people the amount of fluid in the interstitial compartment should be a relatively constant value within a small range. Thus, this value should be the criterion to indicate the degree of a patient's body hydration.

We have found that the refilling volume of a peripheral body segment, such as an arm (upper extremity) or leg (lower extremity), is an important indicator of a dialysis patient's hydration status or dry body weight. In one aspect, the present invention provides a means to separately measure, by segmental bioimpedance analysis (SBIA), the degree of regional body hydration, including fluid volume in the interstitial compartment and the intravascular compartment, in order to determine a patient's fluid status and dry body weight.

One preferred embodiment of the present invention comprises a means to measure the resistivity of a body segment.

Figure 1B:
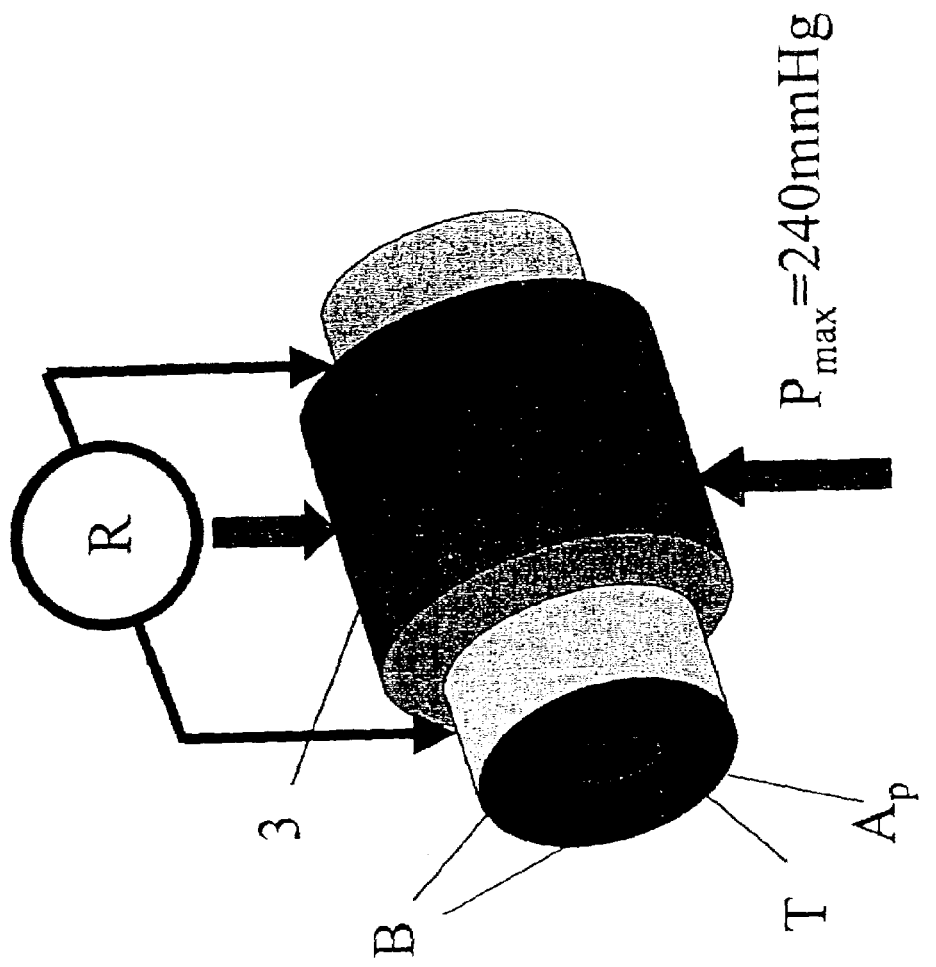
FIGS. 1A and 1B each represent a stylized 3-dimensional view of a body segment, that illustrates the principle of measuring resistivity according to one embodiment of the present invention.
Figure 1A:
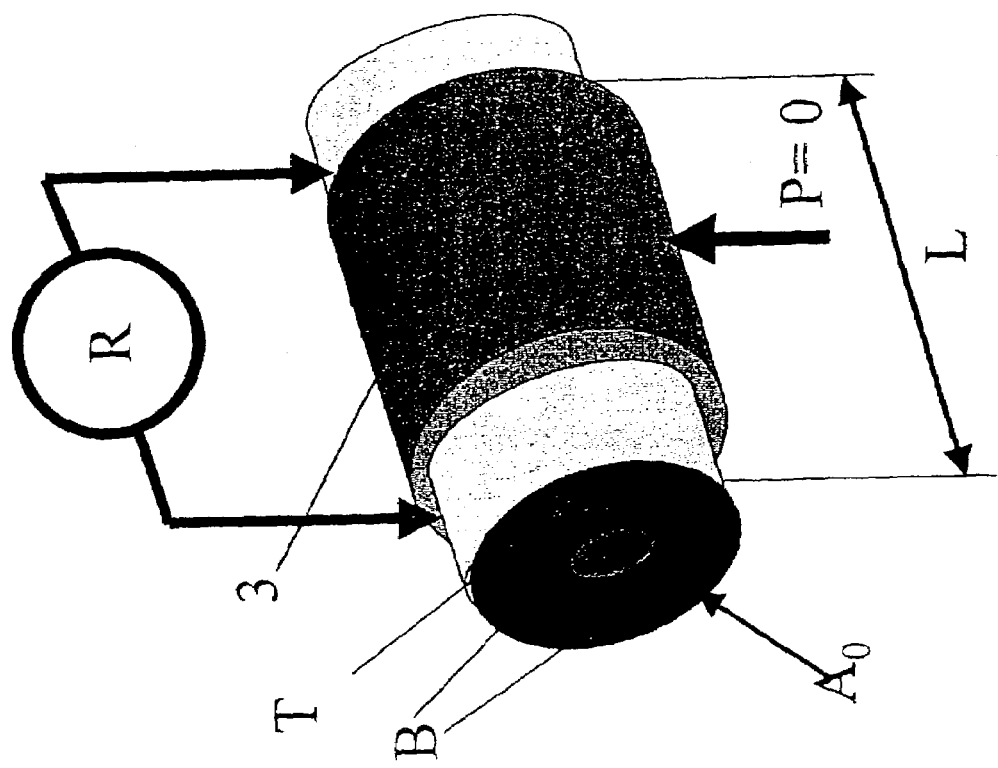

The body segment may be the whole body, preferably a limb segment, more preferably a leg or arm segment, and most preferably a calf segment. As shown in FIG. 1A, the resistivity of a body segment is measured by the placement of measurement electrodes at points L1 and L2, separated by a distance L. One of skill in the art will appreciate that while distance L may vary, it is preferably about 10 cm. The resistivity between L1 and L2 is denoted as R. Also shown in FIG. 1A is a cross-section of the body segment with the interstitial compartment denoted as T and blood vessels denoted as B. Optionally, a means to compress the body segment is provided, for example a pressure cuff 3 that surrounds the body segment. When the body segment is not compressed, for example when the pressure cuff 3 is uninflated, the blood vessels are uncompressed and the resistivity R reflects the resistivity of both the interstitial compartment T and the intravascular compartment B. As shown in FIG. 1B, when the body segment is compressed, for example by inflating the pressure cuff, to a pressure above about the systolic blood pressure, optionally up to about 240 mmHg, the blood vessels are compressed and substantially all of the blood volume contained within the intravascular compartment of the body segment is forced out of the body segment. When the resistivity between the electrodes placed at L1 and L2 is measured under such circumstances, the resistivity value $\rho_I$ represents the resistivity of the interstitial compartment of the body segment.

The principle of measurement of segmental bioimpedance provides a means to measure segmental resistivity and may be explained with reference to FIGS. 1A and 1B. Segmental resistivity is calculated using the formula:

$$\rho_{measure} = AR/L \, (m \cdot \Omega)$$

Where $\rho_{measure}$ is the measured segmental resistivity; A is the cross-sectional area of the segment ($A=C^2/4\pi$, where C is the circumference of the segment). When no pressure is applied to the body segment the cross sectional area $A_0$ represents the cross sectional area of the body segment including that of the blood vessels, when pressure of at least systolic blood pressure is applied the cross sectional area $A_p$ is that of the body segment minus the cross sectional area of the blood vessels; R is resistance as measured by bioimpedance analysis; and L is the distance between the measurement points (i.e. the distance between measurement electrodes).

The measured resistivity of the body segment depends on a number of factors including the frequency of the injected current and the body mass index (BMI). Preferably a single frequency, optionally multiple frequencies (multi-frequencies) are used. Injected frequencies from about 1 kHz to about 1000 kHz, more preferably from about 1 kHz to about 50 kHz, most preferably from about 1 kHz to about 10 kHz are utilized. BMI reflects fat content, and is defined as the body weight in kg divided by the square of the height in meters (weight/height$^2$) and is typically measured in kg/m$^2$. In order to distinguish between intravascular and interstitial fluid, preferably the body segment is compressed, optionally by a pressure cuff, preferably a blood pressure cuff (BP cuff) to produce a pressure (P) sufficient to squeeze blood volume out of the studied segment over a few seconds. Thus, two resistivity values can be measured: $\rho_0$ (uncompressed body segment, P=0 mmHg) and $\rho_p$ (body segment is compressed to a pressure from about systolic blood pressure up to $P_{max}$=240 mmHg).

Based on the resistivity measurement, dry weight and the excess body fluid is calculated according to the equation:

$$\text{Dry weight} = \text{pre-weight} - V_{excess}$$

Where pre-weight is the weight of the patient at a time prior to the completion of dialysis, preferably prior to the initiation of dialysis, and $V_{excess}$ is the excess volume of fluid in a patient's body that must be removed in order to achieve dry weight.

The equation to calculate $V_{excess}$ is:

$$V_{excess} = (k_1/k_2) \cdot \rho_{cal} \cdot BMI_p \qquad \text{(Equation 1)}$$

Where $BMI_p$ is the body mass index (kg/m$^2$) of the dialysis patient, $\rho_{cal}$ is resistivity (m×Ω) which is obtained by the equation as follows:

$$\rho_{cal} = \lambda \cdot BMI_p + 200, \, (m \times \Omega); \qquad \text{Eq.1.1}$$

Where $\lambda$ is the fitting coefficient of resistance/density ($\Omega/(kg/m^3)$) derived from a linear regression equation based on the relationship between BMI and resistivity in healthy subjects; and where $BMI_p$ is the BMI of the patient.

Figure 6:
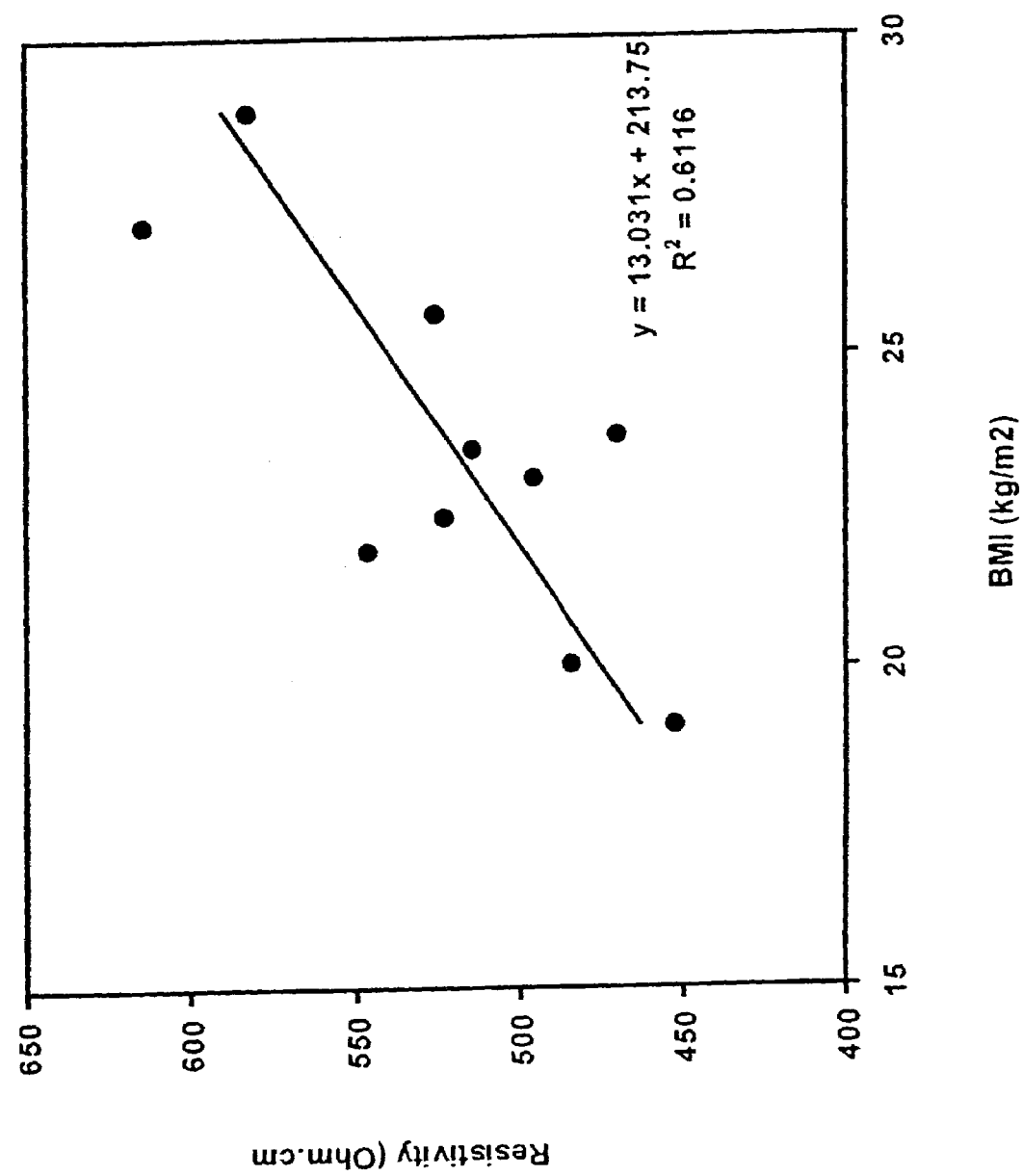
FIG. 6 is a graph of Body Mass Index versus resistivity in a limb segment in ten male healthy subjects.

It is anticipated that specific coefficients will be derived for specific populations for improved results. By way of example, which is not intended to be limiting, utilizing experimental data shown in FIG. 6 from the ten healthy male subjects set forth in Example 1 (below), $\lambda=13$ ($\Omega/(kg/m^3)$). The value of 200 (m·Ω) is the baseline of resistivity when BMI has a minimum value (that must be larger than zero)

$k_1/k_2$ (m/ohm) is a coefficient constant depending on the measurement value according to body geometry and tissue resistivity of the individual patient; and where $k_1 = C_1 \times C_2$ and where $C_1$ is obtained by means of a linear regression equation derived from suitable experimental data correlating the relationship between resistivity of a body segment and clinical dry weight values in dialysis patients; and $$C_2 = \rho_{cal} \times (\rho_{cal} - \rho_{bp})/\rho_{b0}$$

where $\rho_{bp}$ is the resistivity in a body segment of a dialysis patient while the body segment is compressed to a maximum pressure before dialysis, and $\rho_{b0}$ is the resistivity in a body segment of a dialysis patient while the body segment is not at all compressed before dialysis;

Again, it is anticipated that specific coefficients $C_1$ and $C_2$ will be derived for specific populations for improved results.

$K_2$ is the average value for BMI in a population of healthy subjects. In a sample of ten healthy males described in Example 1, the average BMI, $K_2$ is approximately 26.8 kg/m$^2$, and $\rho_{cal}$ is the calculated resistivity (m·Ω)=(13×$BMI_p$)+200 ($\Omega \cdot m^3/kg$)

The measurement system comprises a high speed, low noise, acquisition and multi-frequency bioimpedance measurement unit, such as is known to one of ordinary skill in the art, preferably a Xitron 4200s (Xitron Technologies, San Diego, Calif.). Connected to the bioimpedance measurement unit, the system includes an electrical output means attachable to a body segment, the electrical output means preferably comprising at least two injector electrodes for application to a body segment and for the injection of current into the body segment. The system can apply a single frequency of current, or optionally multiple frequencies of electricity (multi-frequencies) ranging from about 1 kHz to about 1000 kHz, more preferably from about 1 kHz to about 50 kHz, most preferably a single frequency from about 1 kHz to about 10 kHz through the injector electrodes. The system further comprises an electrical input means that is adapted to receive the electrical current transmitted from the output means and through the body segment and to then transmit the current to the bioimpedance analysis measurement unit.

The input means comprises at least two measurement electrodes for application to the body segment for the receiving and transmission, to the BIA measurement unit, of current transmitted through the selected segment. The electrodes may be made of Ag/AgCl film, conductive rubber, or other appropriate materials which are readily apparent to one of ordinary skill in the art. The injector and measurement electrodes are connected electrically to the BIA measurement unit. This electrical connection may be accomplished by a number of means readily apparent to a person of ordinary skill in the art, but preferably by electrical cables.

Figures 10, 10A:
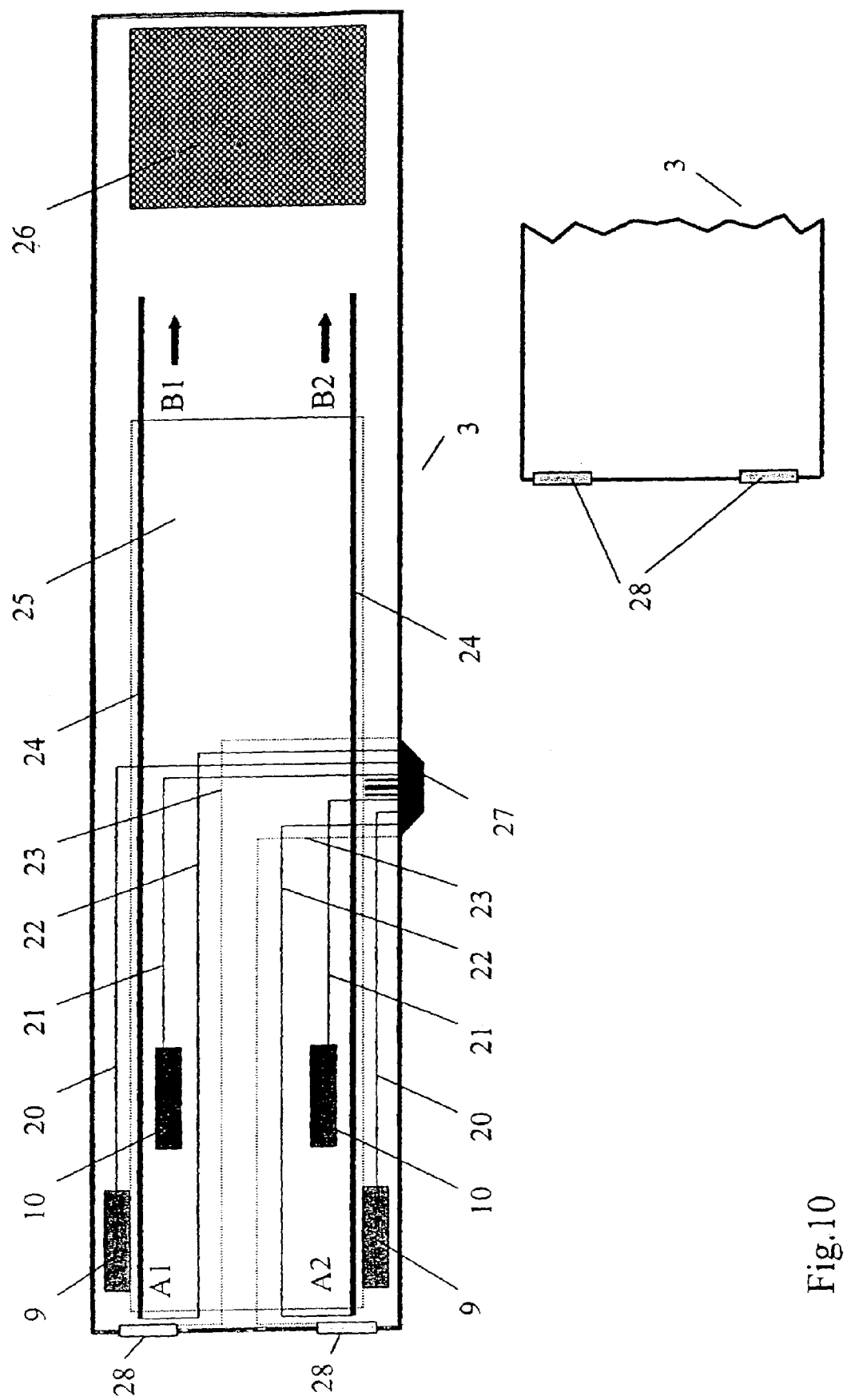
FIG. 10 is a diagram of a pressure cuff for measurement of the circumference of a body segment and for use in measurement of segmental bioimpedance when the body segment is compressed or uncompressed. Shown is a front view with the covering partially cut away, and in FIG. 10A, a partial back view showing the conductive plates.

In one preferred embodiment of the present invention, the electrodes are incorporated into a pressure cuff suitable for surrounding and compressing the body segment. A single cable optionally may incorporate both the electrical wires to the injector and measurement electrodes and the air tubing connected to the pressure cuff. Such a cable is used to connect the pressure cuff to the measuring unit and an optional air pump. Alternatively, separate electrical cables and a separate air hose may be employed. Optionally, the pressure cuff incorporates a means for electrically measuring the circumference of the body segment. An example of a preferred pressure cuff configuration 3, which is not intended to be limiting in any way is disclosed in FIG. 10. The pressure cuff 3 is a blood-pressure cuff type device that comprises a substantially rectangular form suitable for wrapping around a body segment, such that the body segment is encircled by the device. The pressure cuff is composed of a fabric or other flexible material that preferably is capable of being easily cleaned and/or decontaminated. Material that is suitable will be readily apparent to one of ordinary skill in the art. The pressure cuff also includes a means for securing the device on the body segment, such as a Velcro® system or other such securing system 26, as will be readily apparent to one of ordinary skill in the art. Contained within the pressure cuff 3 is a flexible air-bladder 25 or similar means of compressing the body segment, and applying substantially circumferential pressure of at least about systolic blood pressure to the body segment. The air-bladder is connected to an air hose through which air can be moved to inflate or deflate the air-bladder. The pressure cuff preferably includes at least two injector electrodes 9 and at least two measurement electrodes 10 incorporated therein. The injector and measurement electrodes are electrically connected, preferably by electrical wires 20 and 21 respectively, to a cable connector 27, or other means of electrically connecting the pressure cuff 3 to a bioimpedance measurement unit. At least one, preferably two conductive bands 24 extend substantially the length of the pressure cuff, such that the length of the bands is at least equal to the smallest normal body segment circumference. The bands are composed of a material of stable resistivity. Suitable material includes Cu-Sc alloy or conductive rubber. Other suitable material will be readily apparent to one of ordinary skill in the art. The pressure cuff also comprises at least one and preferably two conductive plates 28 located at the end of the pressure cuff opposite to the end with the securing means 26. The conductive bands 24 and conductive plates 28 are electrically isolated from one another and each is connected, preferably by wires 22 and 23, respectively, to a means of measuring resistivity. The band(s) 24 and plate(s) 28 are arranged on the pressure cuff, such that when the pressure cuff is wrapped around the body segment, the plate(s) 28 electrically connects with the band(s) 24 at a location or locations along the length of the belt such that the distance, measured along the length of the pressure cuff, from the plate(s) 28 to the point of contact on the band(s) 24 is substantially equal to the circumference of the body segment. The circumference of the body segment then can be determined electrically according to the equation:

$$L_{b1} = R1 \times A1 / \rho 1$$

Where $L_{b1}$ is the length of the band between the end of the pressure cuff 3 closest to the end where the plate(s) is (are) located and the location at which the plate 28 contacts the band 24;

where R1 is the resistivity of the band between its end closest to the end at which the plate(s) is (are) located and the location at which the plate 28 contacts the band;

where A1 is the cross-sectional area of the band;

and $\rho 1$ is the resistivity of this material.

In this manner, by determining the resistivity of the length of the band(s) that substantially equals the circumference of the body segment, the circumference of the body segment can be determined electrically. In this embodiment, it is preferred that the pressure cuff be securely applied prior to each measurement in order to more accurately measure body segment circumference.

Figure 2:
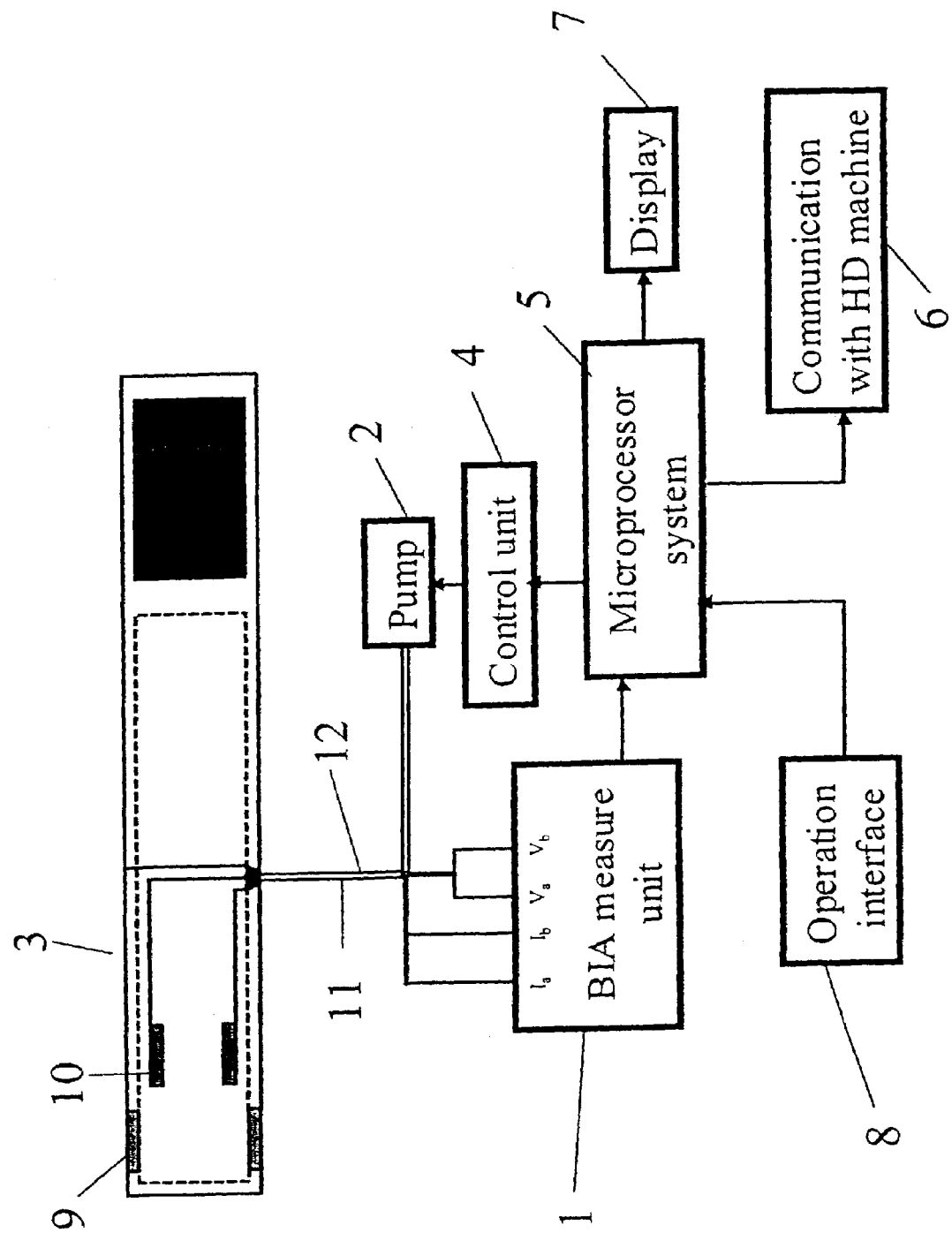
FIG. 2 is a block diagram of a measurement system according to the present invention.

Another embodiment comprises a device for controlling a hemodialysis machine. In this and in other embodiments disclosed herein, an example of a hemodialysis machine suitable for use in or with the invention is that disclosed in U.S. Pat. No. 5,580,460 to Polaschegg. An example, which is not intended to be limiting in any way, is depicted in FIG. 2. In addition to the BIA measurement unit 1, the measurement system also comprises one or more of an air pump 2 to produce pressure to inflate the pressure cuff 3, a control unit 4 to transfer signals from the microprocessor in order to operate the pump, a microprocessor system 5 which is at least a minimal computer with fast data transfer, rapid access and a memory space sufficiently large to permit the manipulation and analysis of the inputted data, a means of communicating with the dialysis machine 6 whereby control signals are sent to and received from the dialysis machine allowing the control of ultrafiltration rate and other hemodialysis parameters according to body hydration status, a display 7 that shows the result of online measurement and an operation interface 8 to input individual patients' parameters to monitor and control dry weight and optionally a means of communication to a standard personal computer (PC) or other device. Optionally, data including, but not limited to, resistance, resistivity, cuff pressure and heart rate is transmitted to the PC by a RS 232 interface or another standard interface in ASCII or other format such that the waveforms of resistivity, pressure values, heart rates and other parameters can be observed, stored, or manipulated on the PC. The block diagram in FIG. 2 shows injector electrodes 9 and measurement electrodes 10, optionally incorporated into the pressure cuff 3. The injector and measurement electrodes are attached, preferably by electrical wiring 11, to the to the output sockets $I_a$ and $I_b$ and input (measurement) sockets $V_a$ and $V_b$ of the BIA measurement unit 1, and the air pump 2 is connected to the pressure cuff by an air hose 12.

In this embodiment, various patient specific parameters are input into the microprocessor system 5 by means of the operation interface 8. Inputted data and other data optionally are displayed in the display 7. The microprocessor system 5 is connected to the BIA measurement unit 1 by a means of transmitting signals to the BIA measurement unit and signaling the BIA measurement unit to send electrical current to the injector electrodes 9. When such an electrical current is sent through the injector electrodes into the body segment, the current is detected by the measurement electrodes and transmitted back to the BIA measurement unit for processing, the derived date being transmitted to the microprocessor system. The microprocessor system is also connected to the pump control unit 4 which is capable of sending signals to the air pump 2 to inflate and deflate the pressure cuff 3, allowing bioimpedance measurements to be made with the pressure cuff inflated and/or deflated. The microprocessor system is also connected to the hemodialysis machine by a communication means 6, whereby signals can be sent to the hemodialysis machine permitting changes in the hemodialysis procedure, such that the patient's hydration status may be altered.

In one embodiment of the present invention, the ultrafiltration rate is varied by the microprocessor in response to on-line monitoring of the patient's segmental resistivity in order to achieve the patient's proper dry weight or other desired hydration status, and to prevent hypotension during hemodialysis. Optionally, the individual ultrafiltration rate is varied using a time course function related to the slope of changes in segmental resistivity (explained below) during dialysis to optimize the hemodialysis treatment.

The present invention provides a means to determine hemodialysis and peritoneal dialysis patients' dry weight to facilitate the appropriate dialysis prescription. In one preferred embodiment of the present invention segmental bioimpedance is continuously measured in a body segment during hemodialysis. The body segment may be any portion of the body or the entire body, but is preferably a limb segment, more preferably a leg or arm segment, most preferably a thigh segment. The relative changes in the value of resistivity is calculated from about every 20 minutes to about every one minute, more preferably about every 10 minutes, even more preferably about every 5 minutes, and most preferably about every minute. The circumference of a body segment, preferably a thigh segment or optionally an arm segment, is measured, preferably at the start, optionally at the end of treatment, and preferably intermittently during dialysis, more preferably from about every 10 minutes to about every 20 minutes, in order to derive the cross-sectional area of the segment. Preferably, at least two injector electrodes and at least two measurement electrodes are attached to the body segment. The electrodes may optionally be incorporated within a pressure cuff 3 in the manner set forth above (see, for example, FIG. 10) applied with a pressure cuff and may more preferably be applied as part of a pressure cuff-electrode combination device.

Periodically, current is injected into the body segment through injector electrodes and the current transmitted through the body segment is received by the measurement electrodes. Current from the measurement electrodes then is transmitted to the BIA measurement unit, which determines the resistance of the body segment and optionally transmits the calculated resistance to a microprocessor system that calculates the resistivity according to the method disclosed herein, and which, in turn, may control a hemodialysis machine. Multiple resistivity data points are obtained over time, a curve is derived, and the slope of the curve determined. The slope of the curve approaching zero indicates that a substantially constant resistivity has been achieved, thereby reflecting that dry weight has been substantially attained. As the resistivity curve slope approaches zero, the hydration status of the patient approaches dry weight. Optionally, ultrafiltration may be prolonged or otherwise modified until dry weight is achieved during the ongoing hemodialysis treatment session or hemodialysis may be prolonged during the next hemodialysis treatment to remove the excess fluid and achieve dry weight.

In another embodiment, suitable for both hemodialysis and peritoneal dialysis patients, comparison of the body segment resistivity, preferably post dialysis resistivity, of dialysis patients to the body segment resistivity of healthy subjects is used to determine the patients' hydration status and optionally the appropriate end point for dialysis. The circumference of a body segment is measured, preferably at the start and optionally at the end of treatment. The body segment may be the whole body, a limb segment such as a leg, arm, or other extremity, and is preferably a thigh segment or an arm segment. Preferably, at least two injector electrodes 9, at least two measurement electrodes 10, and optionally a pressure cuff 3 are attached to the body segment (see, for example, FIG. 10). Preferably, the electrodes are incorporated within to the pressure cuff. At least once, preferably about the time that the dialysis treatment is completed, bioimpedance of the body segment is measured. Optionally bioimpedance is measured at the start and end of the dialysis treatment, periodically, during most or all of the dialysis treatment, optionally from about every 10 minutes to about every 20 minutes. Bioimpedance is measured optionally with the body segment uncompressed or preferably, with the body segment compressed, preferably by inflation of the pressure cuff. The injection and measurement of current is coordinated to correspond with time points when the pressure cuff is substantially fully inflated or substantially deflated.

To measure resistivity, current is injected into the body segment through injector electrodes and the current transmitted through the body segment is received by the measurement electrodes and transmitted to the BIA measurement unit for calculation of the resistivity of the body segment, the derived data optionally being transmitted to the microprocessor system, which, in turn, according to the method disclosed herein.

To obtain a range of normal resistivity values, the bioimpedance of healthy subjects is measured repeatedly at specific body segments, which may be the whole body, preferably a limb segment, more preferably a leg or an arm segment, most preferably a thigh segment, over about 15 minute periods. From these values, a set of normal resistivity values is derived that correlates with dry weights. Preferably a large group of healthy subjects is studied to produce a set of normal resistivity values for a specific population. Optionally, determination of resistivity in subsets of the healthy population can be performed in order to more precisely correlate resistivity values with dialysis patient's dry weight. For example, because fat mass is often an important factor affecting the measurement of body fluid volumes by bioimpedance analysis, mainly due to the association between the conductivity of skin or fat free mass and the amount of fat, stratification of bioimpedance values according to BMI, gender or age optionally may be undertaken.

At any particular time point, the resistivity of the dialysis patient's body segment is compared to the resistivity of the equivalent body segment in healthy subjects, in order to determine the patient's hydration status. When the resistivity of the dialysis patient's body segment is substantially equal to the resistivity in normal subjects, the dialysis patient is determined to be substantially at dry weight, and preferably the patient's body weight is measured. Subsequently, the patient's body weight measured at a different time point can be compared to the body weight measured at the time that the patient was at about dry weight in order to determine $\Delta W$, the difference between the patient's actual weight and dry weight, and thereby the patient's state of hydration.

Using $\Delta W$, the patient's dialysis protocol may be modified so that dry weight is achieved post-dialysis. By way of example, which is not intended to be limiting, if a patient is determined, by comparing resistivity values to those of healthy subjects, to be at dry weight at a mass of X kg, and if at the time of the next dialysis treatment the patient's mass is Y kg and Y>X, then $\Delta W = Y - X$, reflecting the amount of excess fluid to be removed by dialysis to achieve dry weight. Preferably, repeated determinations of dry weight by bioimpedance analysis are performed periodically to provide greater precision in determining the dry weight of a particular patient.

Figure 7:
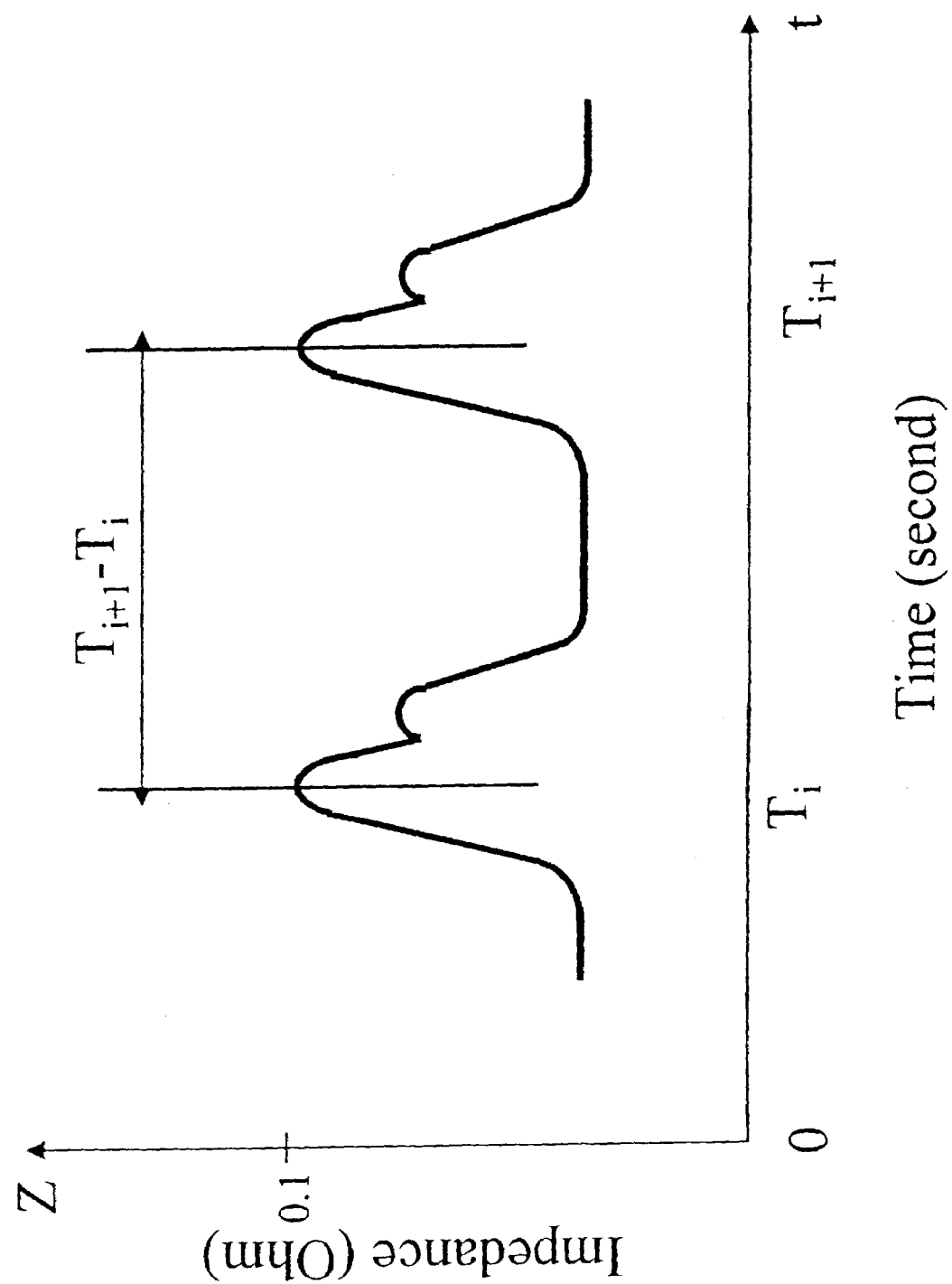
FIG. 7 is a graph showing the change is body segment impedance in relation to the change in body segment blood volume due to arterial pulses.

It is known that the bioimpedance of a body segment changes as the blood pumped by the heart enters and leaves the body segment with each heart beat. By frequent or continuous injection of current and measurement of segmental bioimpedance, a wave form that reflects the pulse can be derived. Based on this information, the present invention provides a means to determine and monitor the heart rate of a patient prior to, during, or after hemodialysis by means of BIA, according to the equation:

$$HR = 60/(T_{i+1} - T_i)$$

where HR is the heart rate in beats per minute; and $T_{i+1} - T_i$ is the time period between peaks of any two successive heart beat induced impedance waves, $T_i$ and $T_{i+1}$, as shown in FIG. 7.

In another embodiment of the invention, BIA is optionally used to determine cardiac output in individuals, including, but not limited to healthy subjects, and dialysis patients prior to, during, or following dialysis. Estimation of CO is based on the assumption that there is a high degree of symmetry in the distribution of blood vessels on both sides of the body and the fact that total blood volume per pulse (stroke volume) can be measured in the segments of the arm ($SV_{arm}$) and leg ($SV_{leg}$) using bioimpedance simultaneously (preferably measuring the stroke volume from an arm and an ipsalateral leg (i.e., on the same side of the body)).

Figure 8:
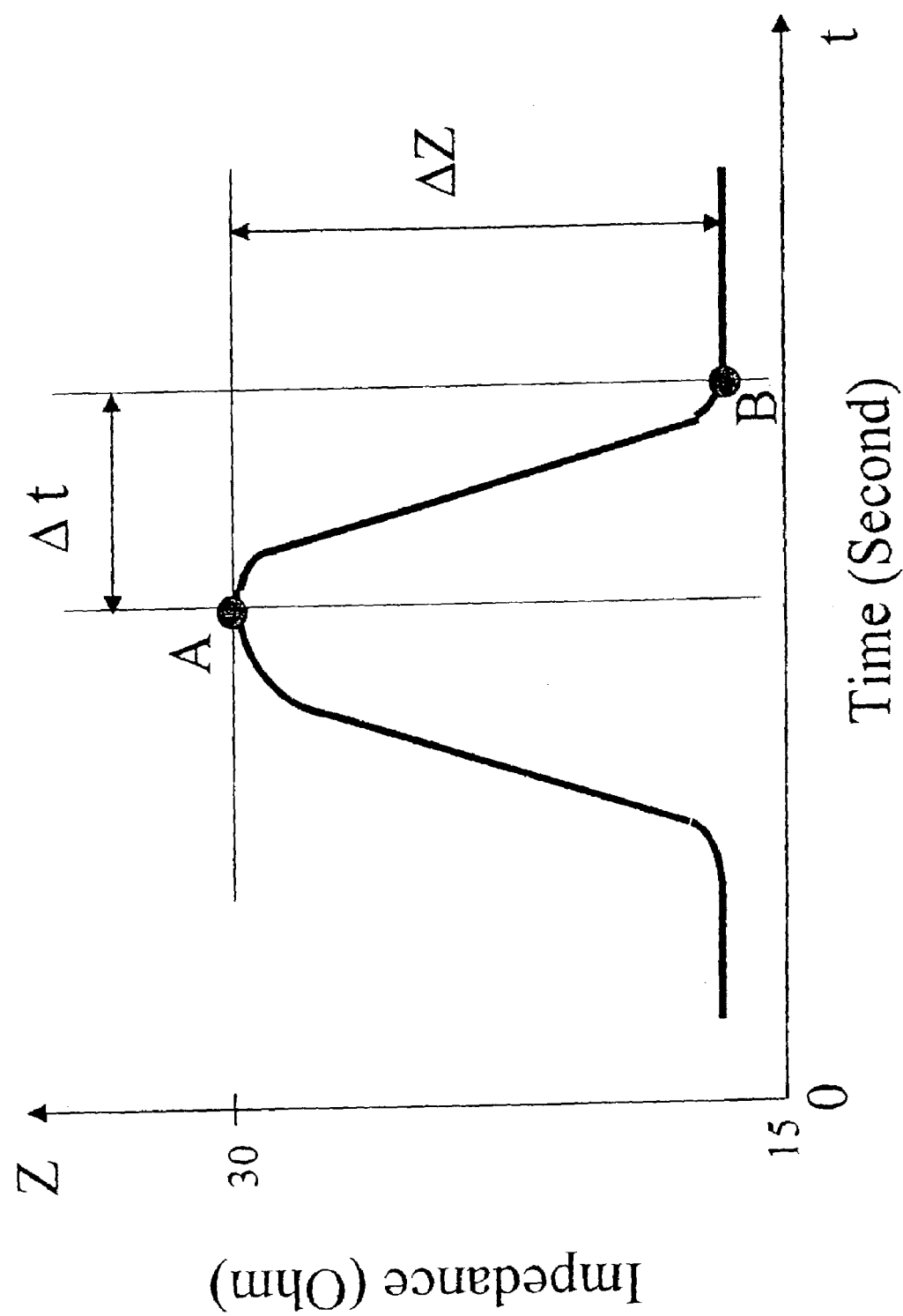
FIG. 8 is a graph showing changes in impedance of a limb segment in relationship to pressure cuff pressure.

The equation used to calculate cardiac output is:

$$CO = 2 \times HR(k_3 \times SV_{arm} + k_4 \times SV_{leg}) (L/min)$$

where $SV_{arm}$ and $SV_{leg}$ are the stroke volume in the arm and in the leg respectively;

$SV_{arm}$ and $SV_{leg}$ are calculated using the following formulas:

$$SV_{arm} = \Delta V_A / N_A \text{ and } SV_{leg} = \Delta V_L / N_L$$

where $\Delta V_A$ is the change in blood volume in the arm and $\Delta V_L$ is the change in the blood volume in the leg between the time point of maximal cuff pressure (shown as segment point A in FIG. 8, during which time substantially all the blood volume is squeezed from the limb segment) and the time point when the pressure cuff is deflated (Shown as point B in FIG. 8, during which time blood volume is refilled by the stroke volume). $N_A$ and $N_L$ are the number of pulses during changes in impedance from peak point (A) to baseline (B) respectively.

The values for $\Delta V_A$ and $\Delta V_L$ are calculated as follows:

$$\Delta V_A = -\rho_b L^2 \Delta Z_A / Z_A^2 \text{ and } \Delta V_L = -\rho_b L^2 \Delta Z_L / Z_L^2 \qquad \text{Equation 2}$$

where $\rho_b$ is the resistivity of blood, L is the length of the body or limb segment between the electrodes, and $Z_A$ and $Z_L$ are each respective impedance values. Calculations of $\Delta V_A$ and $\Delta V_L$ are performed according to the method of J. G. Webster in, *Medical Instrumention Application and Design*, 3rd Ed., Wiley, N.Y., 1998 pp. 357–362, which is hereby incorporated herein by reference, in its entirety.

The coefficients $k_3$ and $k_4$ are coefficients of calibration for individuals in $\Delta V_A$ and $\Delta V_L$ respectively. The calibration is performed by injecting from about 5 ml to about 150 ml into a vein distal to the arm segment in which resistivity is to be measured, while the resistivity is measured continuously in the arm segment. As the wave of increased volume ($\Delta V$) passes through the segment, there is a change in resistance ($\Delta R$) in relation to the volume injected. Using the relationship between $\Delta V / \Delta R$, $k_3$ and $k_4$ are calibrated.

The calibrating process provides the information about how a change in resistance per ohm is related to a known change in volume ($\Delta V / \Delta R$). By definition, define $k_c = \Delta V / \Delta R$ as a calibration coefficient, where $\Delta V$ is the volume of injected saline (ml) and $\Delta R$ is the change in resistance in the calibrating segment. Thus, $k_3$ is defined by equation as follows:

$$k_3 = k_c \times \Delta Z_A / (N_A \times V_A)$$

Where $\Delta Z_A$ is the change in impedance in the arm, $V_A$ is volume calculated by set, and $N_A$ is number of pulses. Similarly, the equation $k_4 = k_c \times \Delta Z_L / (N_L \times V_L)$ is used to calibrate for changes in the volume of a leg.

Figure 11:
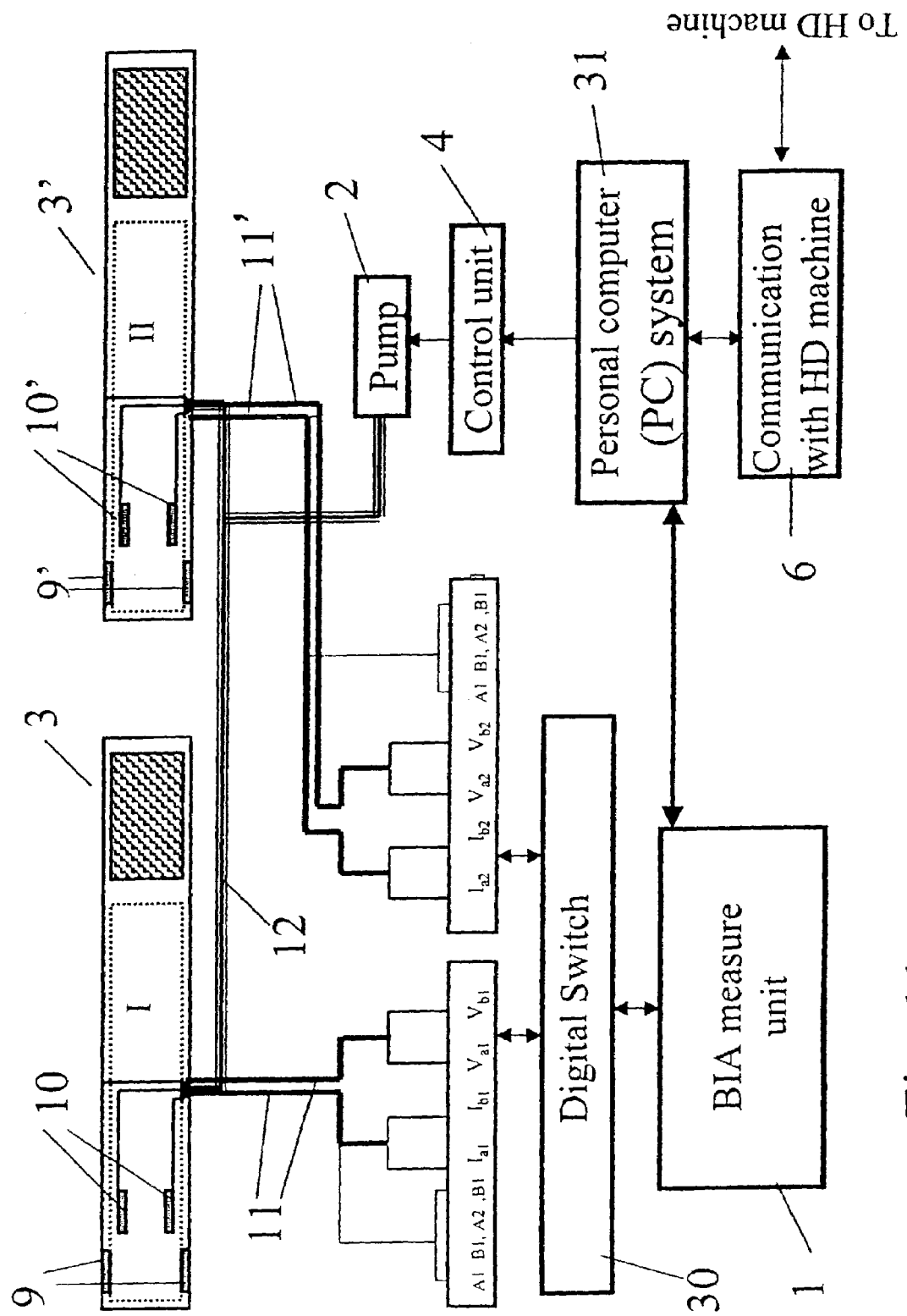
FIG. 11 is a block diagram of a device according to the present invention that also provides a means for determining cardiac output.

One embodiment of a system such as that disclosed in FIG. 2, but additionally being capable of measuring cardiac output is shown in FIG. 11. Included are two sets of electrodes 9 and 10 and 9' and 10', preferably incorporated into two pressure cuffs 3 and 3' adapted to be attached to a leg segment (not shown) and to an ipsalateral arm segment (not shown), both sets of electrodes being connected to a digital switch, via wiring 11 and 11', capable of rapidly switching between each set of electrodes, so that measurements may be taken from either the leg segment or the arm segment substantially simultaneously. Preferably the digital switch 30 has the capacity to achieve a sampling frequency of at least about 200 Hz and, more preferably, greater than 1 kHz. Optionally, there is a means to send a control signal from a computer 31 to the digital switch so that the sample frequency can be changed as needed.

Figure 12:
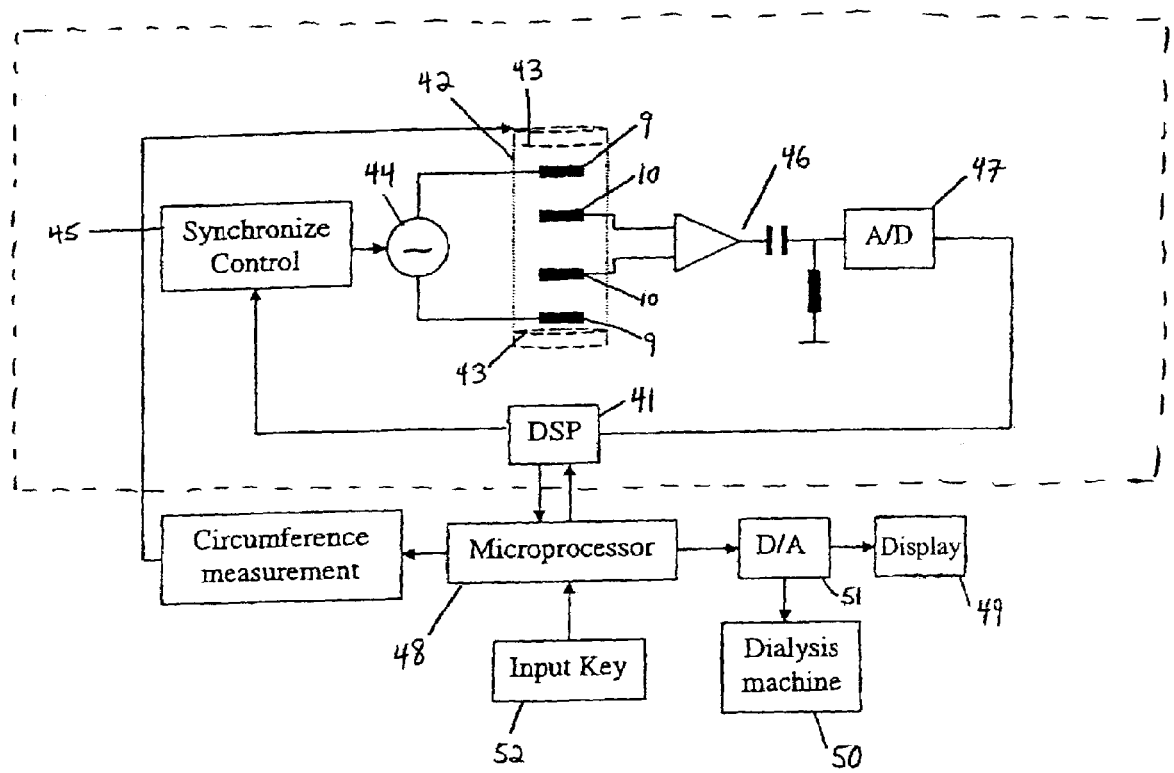
FIG. 12 is a block diagram of a measurement device according to the present invention.

Another embodiment of the present invention comprises a separate device for monitoring the hydration status in a hemodialysis patient, which continuously measures changes in regional resistance and resistivity in a body segment, such as an arm, leg or trunk. Such regional resistance and resistivity measurements are used as a means of assessing change in the extracellular volume using bioimpedance techniques during hemodialysis treatments. A representative example of the device is depicted in FIG. 12. As can be seen in FIG. 12, the device includes: injector electrodes 9 and measurement electrodes 10, each integrated into an electrodes pad 42, which is made from regular adhesive material and contains two conductive wires 43 used to measure segmental circumference; a digital signal processor (DSP) 41 which generates alternate current with different frequencies to be sent to the injector electrodes 9, and pre-processes data from the measurement of voltage from the measurement electrodes 10; a current source 44 which generates different frequencies injected at constant current to the injector electrodes 9; a synchronized control circuit 45 used to synchronize the phase between the current and voltage measured; a measuring circuit 46 which includes amplifier and filter circuits for measuring voltage from the measurement electrodes 10; an A/D converter 47 which converts an analog signal to a digital signal; a microprocessor 48 comprising at least a minimal computer with fast data transfer, rapid access and a memory space sufficiently large to permit the manipulation and analysis of the inputted data, which receives data, calculates, sends results to a display 49, and provides feedback to a dialysis machine 50; a D/A converter 51 which converts a digital signal to an analog signal; a display 49, such as, for example, an LCD display, for displaying the results of online measurement; an input key 52 for inputting individual patients' information for individual treatment; and a dialysis machine 50 which receives and sends control signals allowing for the control of ultrafiltration rates and volumes. In this representative embodiment depicted in FIG. 12, data is transported via the customary means of an electronic patient's cable which connects to injector electrodes 9 and measurement electrodes 10 within the electrode pad 42 on the patient's skin and transports a signal to the DSP 41 and the microprocessor 48 (i.e., through the device), wherein the device itself may be placed within the dialysis machine or may stand alone. When measuring the segmental circumference using the representative embodiment depicted in FIG. 12, the segmental circumference is measured using the same basic principles as were employed when measuring the segmental circumference using the pressure cuff embodiment, as was previously described herein. That is, the segmental circumference (i.e., the circumference of the body segment) is determined electrically according to the equation:

$$L = R \times A / \rho;$$

where L is the length of the conductive wire 43; R is the resistance of the conductive wire 43; A is the cross-sectional area of the conductive wire 43; and $\rho$ is the resistivity of the conductive wire 43.

An alternative representative embodiment of the device for continuously measuring changes in regional resistance and resistivity in a body segment is represented by the dotted line in FIG. 12. That is, this device may also be self-contained within a single unit. The dotted line in FIG. 12 can represent an electrode pad into which the device elements required for measurement (including the measuring circuit 46, the A/D converter 47, and the DSP 41) are fully integrated. Then, digital signals are sent by a cable from this fully integrated electrode pad to another element of the device which is placed in the dialysis machine for further signal processing.

This device according to the present invention is used to monitor the hydration status in a hemodialysis patient, and/or to determine a patient's dry weight. The continuous measuring of changes in regional resistance and resistivity in a body segment, such as an arm, leg or trunk, are used as a means of assessing change in the extracellular volume using bioimpedance techniques during hemodialysis treatments. Specifically, the relative changes in extracellular volume (ECV) in the regional body segment are calculated according to the following equation:

$$\delta = ECV_t / ECV_0 = (\rho \times L^2 / R_t) / (\rho \times L^2 / R_0) = R_0 / R_t \qquad \text{Equation 3}$$

where $ECV_t$ is a variable equal to the resistivity ($\rho$) times the square of the segmental length (L) divided by the resistance ($R_t$) during hemodialysis; $ECV_0$ is a constant value equal to the extracellular volume at the beginning of dialysis. As shown by Equation 3 above, relative changes in the percentage of ECV can be represented by the changes in the ratio of the resistance $R_0$ at the beginning of hemodialysis to the resistance $R_t$ during hemodialysis.

The regional resistivity p is calculated according to the following equation:

$$\rho = R \times A / L (\Omega \text{cm}), \qquad \text{Equation 4}$$

where R is the extracellular resistance between two measurement electrodes 10; A is the cross sectional area of the regional segment in the body ($A = C^2 / 4\pi$, where C is the circumference of the segment); and L is the length of the segment between two measurement electrodes 10.

The limitation of the refilling rate threshold is defined as the minimum change in the slope of the curve of $\delta$ according to the following equation:

$$\Delta \delta = (R_0 / R_t - R_0 / R_{t+1}) * 100\% \qquad \text{Equation 5}$$

where $\Delta \delta$ is the relative change in the extracellular volume (ECV) during dialysis; R is the resistance during dialysis at time 0 (i.e., the beginning of dialysis); $R_t$ is the resistance during dialysis at time t; and $R_{t+1}$ is the resistance during dialysis at time t+1. Based on the experimental data as described in Example 5, an individual patient should reach his dry weight when $\Delta \delta \leq$ about 2%.

However, an additional step needs to be taken to confirm that the patient has indeed reached his dry weight. Besides a patient reaching his dry weight, there are other reasons for and causes of a change in $\delta$ during dialysis treatment, such as a change in the diameter of vessels in the particular body segment or a variation in cardiac output. Therefore, the measurement of resistivity is necessary to confirm that the patient's dry weight has been reached by comparison with the normal range of resistivity. If and when a patient reaches his dry weight, the resistivity should be represented by the following equation:

$$\text{Resistivity } (\rho) \geq \rho N \qquad \text{Equation 6}$$

where $\rho N$ is the normal range of resistivity ($\rho N = 591 \pm 89$ ($\Omega$cm) according to previous work (see Zhu et al., *Determination of dry weight in hemodialysis patients by monitoring changes in the slope of extracellular volume (ECV) during dialysis*, ASAIO 48:180 (2002)).

Thus, one embodiment for determining the dry weight of a hemodialysis patient according to the present invention is as follows: calculate $\Delta \delta$ until $\Delta \delta$ is $\leq$ about 2%; then compare $\rho$ to $\rho N$, and if $\rho < \rho N$, then the ultrafiltration rate and treatment time need to be adjusted until $\rho \geq \rho N$, and if $\rho \geq \rho N$, then the dry weight of the hemodialysis patient has been reached. The methods and procedures for adjusting the ultrafiltration rate and treatment time are known in the art and would be understood by one of ordinary skill in the art.

EXAMPLES

Listed below are a series of examples of the present invention. The examples contained herein are intended to illustrate, but are not intended to limit the scope of the invention.

Example 1

Twenty healthy subjects (Table 1) and thirteen hemodialysis patients (Table 2) were studied, the latter during hemodialysis. Shown in Tables 1 and 2 are their mean ages, weights and body mass indices (BMI). Data are presented as mean value±SD

TABLE 1

Healthy subjects

|   | n | Age (years) | Weight (kg) | BMI (kg/m²) |
|---|---|---|---|---|
| Male | 10 | 40.8 ± 5 | 83.1 ± 21.6 | 27.1 ± 5.0 |
| Female | 10 | 35 ± 9 | 64.3 ± 9.7 | 24.2 ± 3.2 |

TABLE 2

Hemodialysis patients

|   | n | Age (year) | Dry Weight (kg) | BMI (kg/m²) |
|---|---|---|---|---|
| Male | 10 | 48.5 ± 12.8 | 76.8 ± 16.4 | 26.8 ± 4.3 |
| Female | 3 | 65 ± 14 | 60.5 ± 16 | 23.7 ± 3.5 |

Example 2

Figure 3:
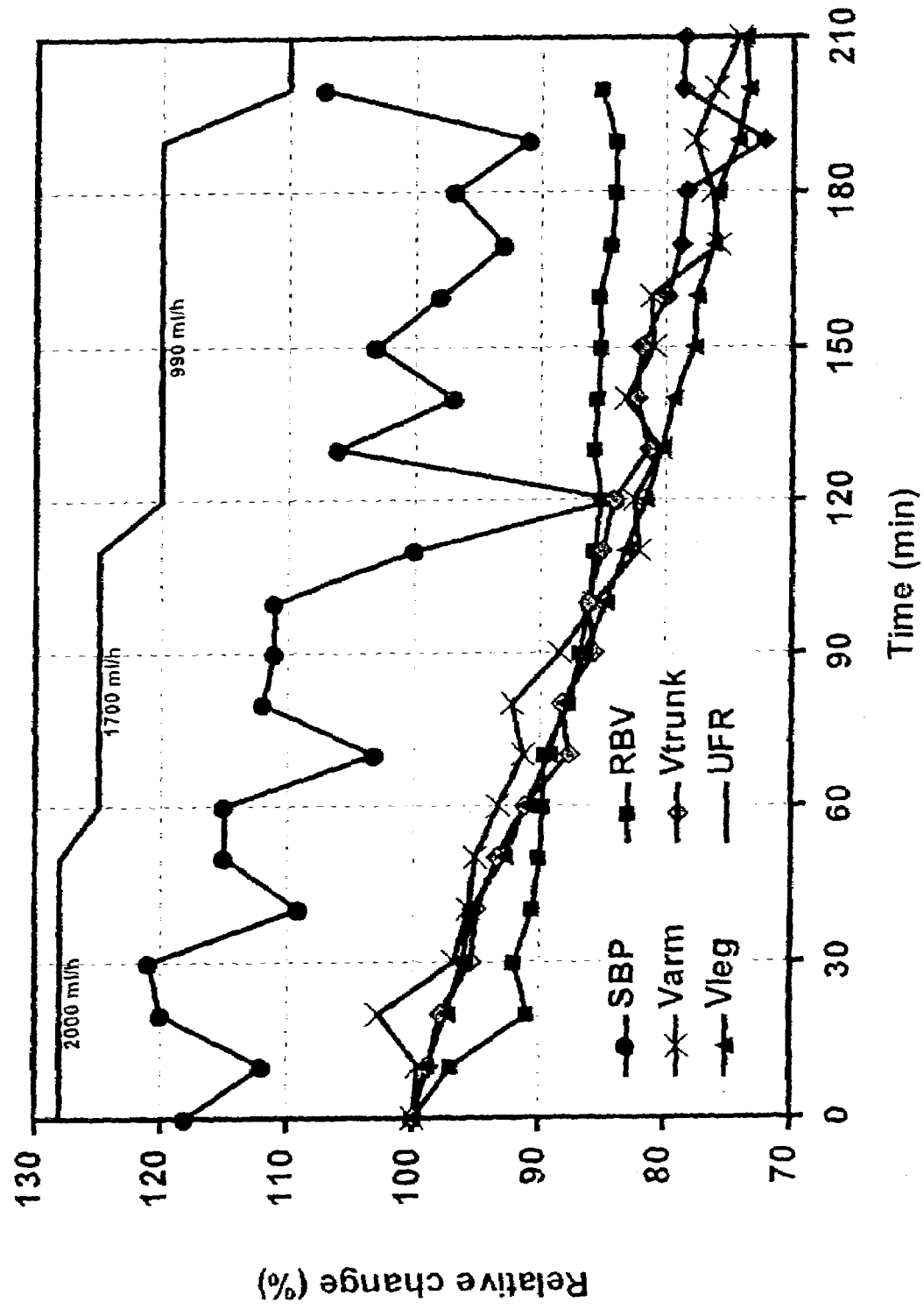
FIG. 3 is a graph of relative changes in systolic blood pressure, ultrafiltration rate, resistivity of different body segments, and relative blood volume over time during hemodialysis.

Segmental bioimpedance was measured continuously every 10 minutes during hemodialysis using 6 electrodes all on the left side of the body. Two electrodes, one on the hand and one on the foot, were used to inject current. Measurement electrodes were placed on the wrist, shoulder, hip and ankle. Resistivity was measured in the wrist-shoulder segment (Varm), the shoulder-hip segment (Vtrunk), and in the ankle-hip segment (Vleg). Also measured were systolic blood pressure (SBP), relative blood volume or hematocrit (RBV), and the ultrafiltration rate (UFR). In this way, blood volume and segmental extracellular volume (ECV) in the leg, arm and trunk were calculated. The results are shown in FIG. 3. The X-axis is time in minutes, the Y-axis the relative change in value with the value of a particular parameter at the start of hemodialysis being equal to 100%. After continuing ultrafiltration changes in ECV of the leg became small that the slope was nearly horizontal i.e. approached 0, which indicates that little fluid was available for ultrafiltration and dry weight had been achieved. Comparing the curves of ECV trunk, leg and arm, it can be seen that the leg is the preferred body segment for dry weight analysis.

Example 3

The resistance and resistivity of a limb segment with and without inflation of a pressure cuff was measured at the start and at the completion of a hemodialysis treatment and ΔW was calculated. Table 3 shows that in a series of patients ΔW was ≠0 at the end of hemodialysis, indicating that these patients were not at their clinical dry weight at the end of hemodialysis.

Figure 4:
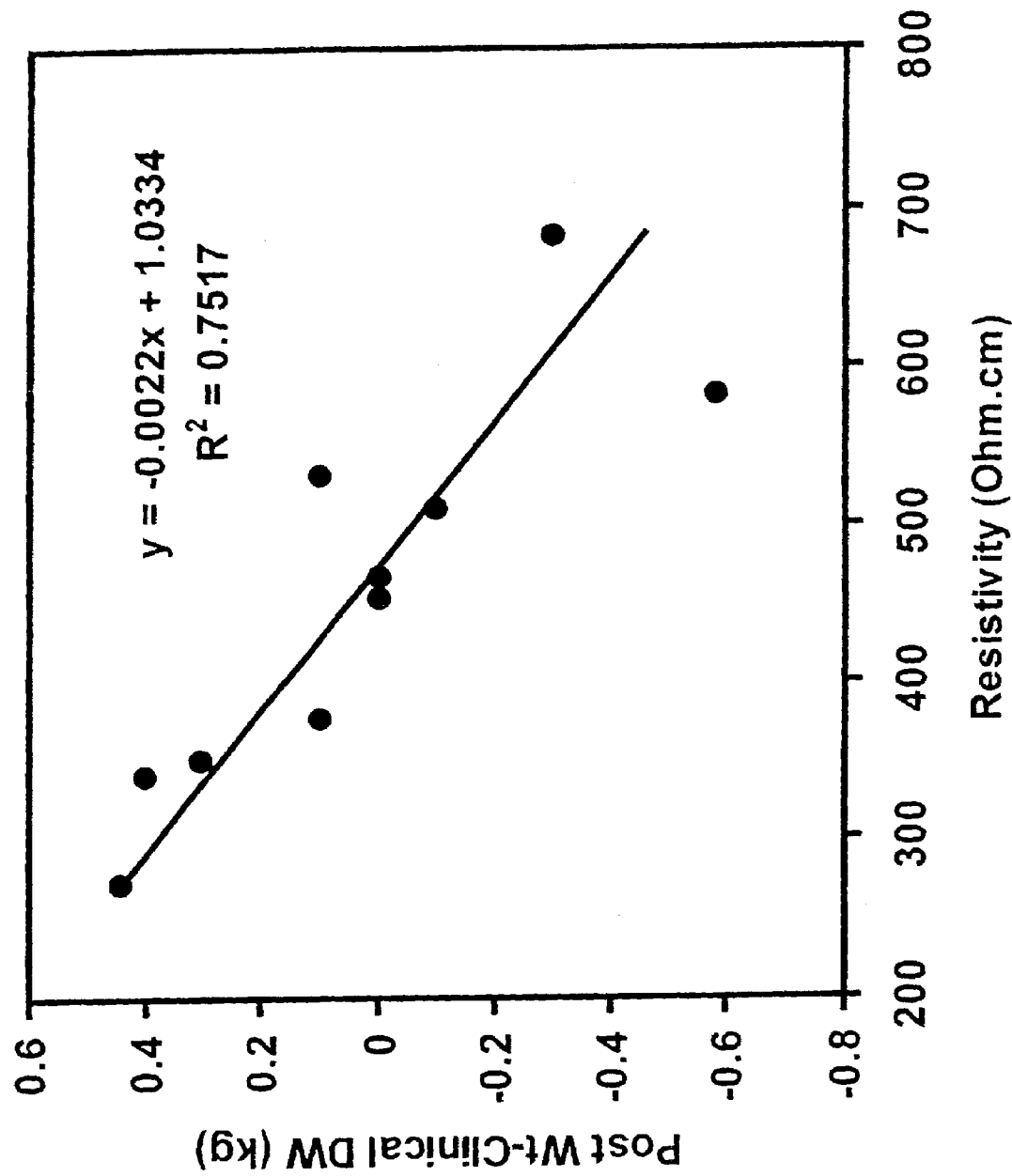
FIG. 4 is a graph of post-dialysis resistivity compared to dry weight in ten male hemodialysis patients.

In confirmation (FIG. 3) both $\rho_0$ and $\rho_p$ at the end of HD were lower or higher in patients than in healthy subjects. This indicates that most patients were overhydrated (i.e., excess fluids were not removed) while some were dehydrated by the treatment and had lower than normal fluid volume. It is a purpose of the present invention to have all patients in substantially the same range as healthy subjects after treatment (note resistivity is inversely related to interstitial volume). FIG. 4 shows a high correlation between ΔW and $\rho_p$ which indicates that $\rho_p$ is capable of being used for analysis of patients' segmental hydration so that dry weight could be predicted by this technique.

Example 4

Figure 5:
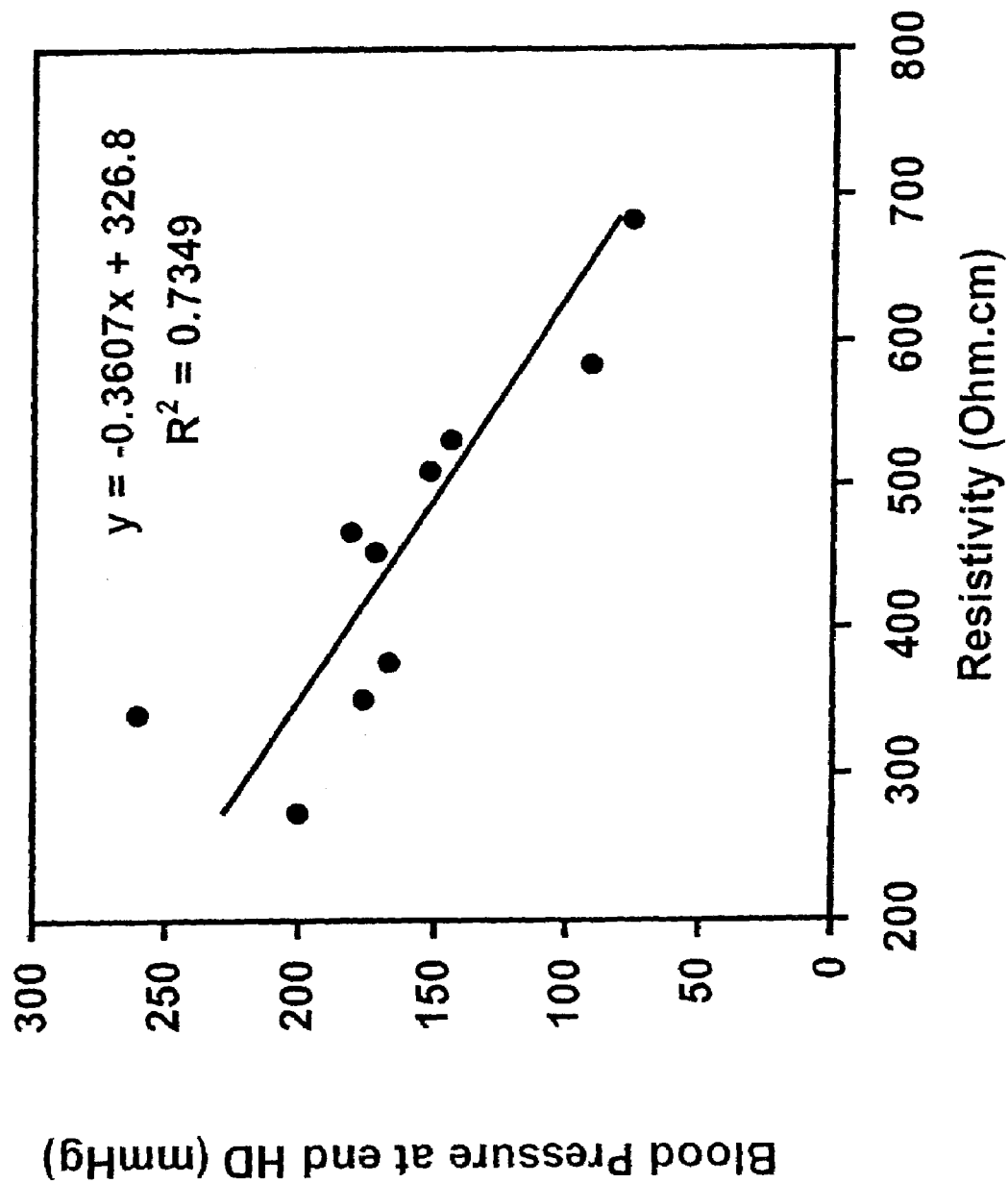
FIG. 5 is a graph showing the relationship between blood pressure and resistivity of a limb segment in ten male hemodialysis patients at the end of hemodialysis.
Figure 9:
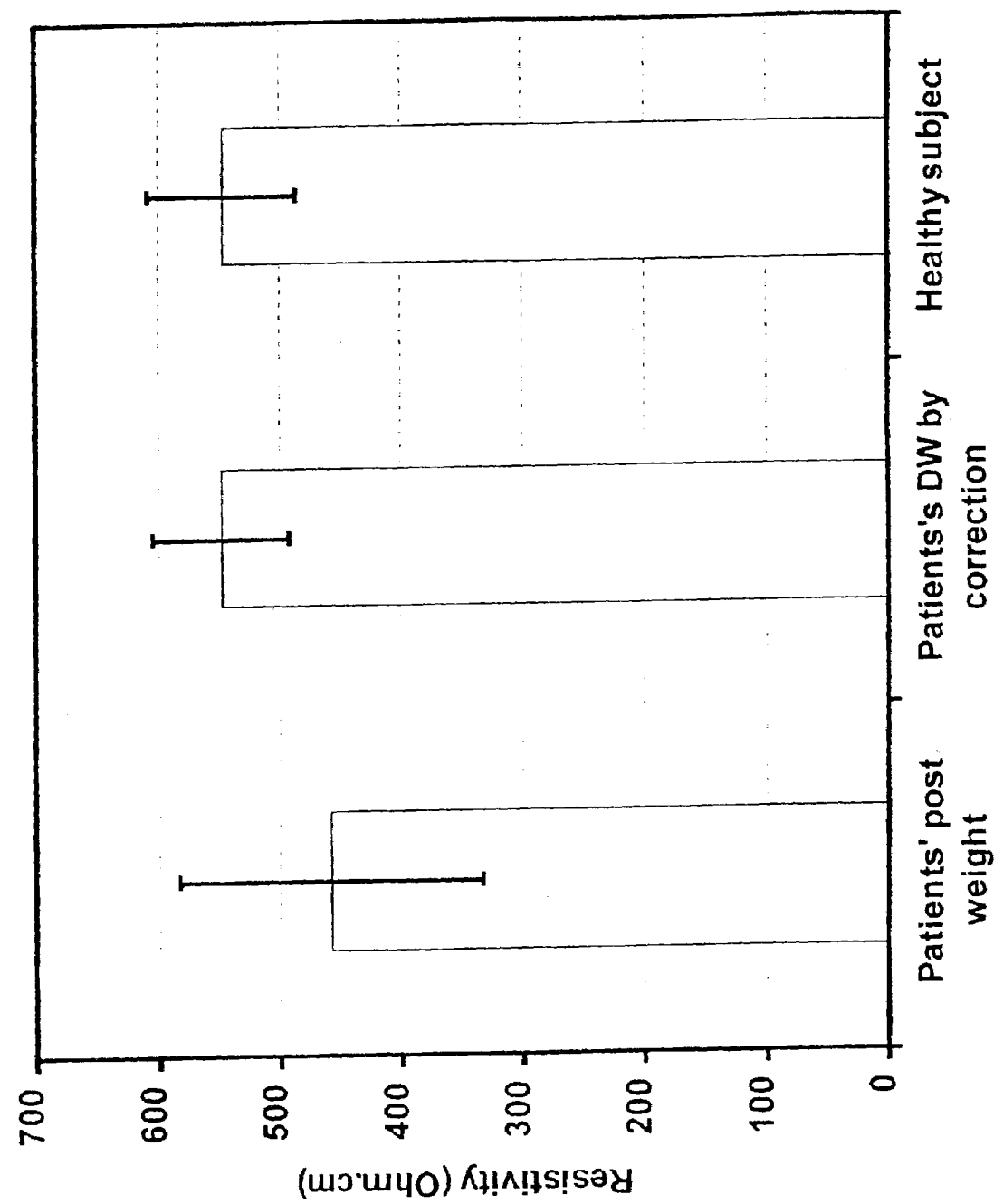
FIG. 9 is a bar graph showing the correlation between a series of ten male hemodialysis patients' post dialysis limb segment resistivity, with and without correction for dry weight, and the limb segment resistivity in a series of ten healthy male subjects.

FIG. 5 shows the clinical correlation of resistivity and blood pressure at the end of hemodialysis in 10 male patients. FIG. 4 shows the clinical correlation between resistivity and body hydration at the end of hemodialysis in these patients. The normal range for resistivity is shown as a solid line. The results demonstrate that the hemodialysis patients were not at the correct dry body weight as indicated by this technique at the end of the treatment. Most were over-hydrated, however the three denoted by the symbol ○ were underhydrated. Using Equation 1 the individual dry weight was calculated according to the healthy subjects' $\rho_0$ and $\rho_p$ and BMI. The patients' dry weight after correction compared to healthy subjects and uncorrected dry weight are shown in FIG. 9.

Example 5

In this example, we studied 21 hemodialysis patients, dividing them into two groups by clinical estimation of whether they were at clinical dry weight (CDW; number of patients=10, mean age=56.6 years) or were over hydrated (OH; number of patients=11, mean age=66.5 years) (see Table 4 below). For each hemodialysis patient, we measured the resistivity and the rate of change in resistance (Δ slope, or Δδ) during a dialysis session, for a particular body segment. The ratio of regional extracellular volume (ECV) was measured by segmental bioimpedance and compared to regional geometric volume (RGV) for estimation of regional hydration (wherein RGV=cross sectional area (A)·length (L, 10 cm)). Our results, as shown in Table 4 below, indicate that the overhydrated patients (OH) had significantly lower resistivity than the clinical dry weight patients (CDW); however, the rate of change in resistance (Δ slope) during dialysis was not significantly different between the overhydrated patients (OH) and the clinical dry weight patients (CDW). We then adjusted the dry weight target in the clinical dry weight patients (CDW) and measured the resistivity as well as the rate of change in resistance (Δ slope) during a subsequent dialysis treatment designed to remove more fluid. The

TABLE 3

Results in ten male patients and ten male healthy subjects

| Subjects | Area (cm²) | $R_0$ (Ω) | $R_p$ (Ω) | $\rho_0$ (Ωcm) | $\rho_p$ (Ωcm) | ΔW (L) |
|---|---|---|---|---|---|---|
| Start HD | 86.7 ± 20 | 41.1 ± 6.7 | 44.3 ± 8 | 354.8 ± 95 | 383 ± 106 | 4.31 ± 1.3 |
| End HD | 81 ± 19 | 53.1 ± 8.4 | 56.6 ± 9 | 428.6 ± 116 | 457.6 ± 125 | 0.17 ± 0.41 |
| Healthy | 98.2 ± 26 | 49.6 ± 10 | 54.5 ± 11 | 500.3 ± 60 | 547 ± 60 | 0 | resistivity increased further and Δ slope decreased by half an order of magnitude, accompanied by a significant decrease in blood pressure, weight and ratio of regional extracellular volume to regional geometric volume (ECV/RGV). Although resistivity increased significantly in the CDW patients following further ultrafiltration, both of these values for resistivity were not significantly different from normal (580±60 ohm·cm). Therefore, it appears that measurement of the rate of change in resistance (Δ slope) is superior to an absolute measurement of resistivity in determining when dry weight is achieved. This suggests that objective dry weight could be identified for individual patients by measuring the rate of change in resistance during dialysis treatments providing a segmental-bioimpedance dry weight (BIA-DW), a weight corresponding to a more normal state of hydration. That is, the CDW group, which hadn't quite reached dry weight, had a Δ slope value of 2.3±0.21%, or 2.09% to 2.51%. Therefore, if a patient had reached his dry weight, the Δ slope value should be less than or equal to about 2%.

TABLE 4

Hemodialysis patients

| | $\rho$ (Ω·cm) | Post ECV/RGV (L/cm³) | Δ slope (%) | ΔRBV (%) | Pre-MAP (mm Hg) | Post-Wt (kg) |
|---|---|---|---|---|---|---|
| OH | 383.4 ± 134 | 0.25 ± 0.08 | 2.2 ± 0.6 | 109 ± 13 | 86.3 ± 10 | 66.2 ± 11 |
| CDW | 524.6 ± 113 | 0.19 ± 0.03 | 2.3 ± 0.21 | 123 ± 19 | 97 ± 15 | 89.6 ± 28 |
| BIA-DW | 609.8 ± 153 | 0.17 ± 0.03 | 0.73 ± 0.5 | 118 ± 16 | 93.6 ± 12 | 88.3 ± 28 | wherein: RBV is relative blood volume; and MAP is mean arterial pressure.

Throughout this application, various articles and patents are referenced. Disclosures of all of these publications are hereby incorporated herein by reference in their entireties. The present invention may be embodied in other forms without departing from the spirit or essential attributes thereof and accordingly reference should be made to the claims rather than to the foregoing specification as indicating the scope thereof

We claim:

1. A device for monitoring hydration status in a hemodialysis patient comprising:
   a digital signal processor;
   an electrical output means being in electrical communication with the digital signal processor and being attachable to a body segment, the electrical output means being adapted to apply electrical current to the body segment;
   an electrical input means being in electrical communication with the digital signal processor and being attachable to a body segment, the electrical input means being adapted to receive the current transmitted through the body segment and transmit the same to the digital signal processor; and
   a microprocessor being in electrical communication with the digital signal processor;
   wherein the microprocessor is adapted to determine a relative change in extracellular volume in the body segment based on a change in resistance in the body segment, and to plot said relative change as a function of time ; and
   wherein the microprocessor determines the relative change in extracellular volume in the body segment according to the following equation:

$$\delta = ECV_t/ECV_0 = (\rho \times L^2/R_t)/(\rho \times L^2/R_0) = R_0/R_t$$

wherein $\delta$ is the relative change in extracellular volume in the body segment, $ECV_t$ is a variable equal to the resistivity ($\rho$) times the square of the length of the body segment (L) divided by the resistance ($R_t$) during hemodialysis, and $ECV_0$ is a constant value equal to the resistivity ($\rho$) times the square of the length of the body segment (L) divided by the resistance ($R_0$) at the beginning of dialysis.

2. A device for determining the dry weight of a hemodialysis patient comprising:
   a digital signal processor;
   an electrical output means being in electrical communication with the digital signal processor and being attachable to a body segment, the electrical output means being adapted to apply electrical current to the body segment;
   an electrical input means being in electrical communication with the digital signal processor and being attachable to a body segment, the electrical input means being adapted to receive the current transmitted through the body segment and transmit the same to the digital signal processor; and
   a microprocessor being in electrical communication with the digital signal processor;
   wherein the microprocessor is adapted to determine the dry weight of a hemodialysis patient based on a relative change in extracellular volume in the body segment.

3. The device of claim 2, wherein the microprocessor determines that the dry weight of a hemodialysis patient has been reached when:

$$\Delta\delta = (R_0/R_t - R_0/R_{t+1}) * 100\% \leq \text{about } 2\%$$

wherein $\Delta\delta$ is the relative change in the extracellular volume (ECV) during dialysis, $R_0$ is the resistance during dialysis at time 0; $R_t$ is the resistance during dialysis at time t; and $R_{t+1}$ is the resistance during dialysis at time t+1; and when resistivity $(\rho) \geq \rho N$ wherein $\rho N$ is a normal range of resistivity.

4. The device of claim 2, wherein the microprocessor determines that the dry weight of a hemodialysis patient has been reached when:

$$\Delta\delta = (R_0/R_t - R_0/R_{t+1}) * 100\% \leq \text{about } 2\%$$

wherein $\Delta\delta$ is the relative change in the extracellular volume (ECV) during dialysis; $R_0$ is the resistance during dialysis at time 0; $R_t$ is the resistance during dialysis at time t; and $R_{t+1}$ is the resistance during dialysis at time t+1.

5. A method for determining a hemodialysis patient's dry weight comprising the steps of:
   periodically measuring the resistance of a body segment during hemodialysis;

comparing successive resistance measurements according to the equation $$\delta = ECV_t/ECV_0 = (\rho \times L^2/R_t)/(\rho \times L^2/R_0) = R_0/R_t;$$

wherein $\delta$ is the relative change in extracellular volume in the body segment, $ECV_t$ is a variable equal to the resistivity ($\rho$) times the square of the length of the body segment (L) divided by the resistance ($R_t$) during hemodialysis, and $ECV_0$ is a constant value equal to the resistivity ($\rho$) times the square of the length of the body segment (L) divided by the resistance ($R_0$) at the beginning of dialysis; and identifying the hemodialysis patient's dry weight when a substantially constant resistivity is reached wherein $$\Delta\delta = (R_0/R_t - R_0/R_{t+1}) * 100\% \leq \text{about } 2\%$$

wherein $\Delta\delta$ is the relative change in the extracellular volume (ECV) during dialysis; $R_0$ is the resistance during dialysis at time 0; $R_t$ is the resistance during dialysis at time t; and $R_{t+1}$ is the resistance during dialysis at time t+1.

6. The method of claim 5, wherein identifying the hemodialysis patient's dry weight further comprises when resistivity $(\rho) \geq \rho N$, wherein $\rho N$ is a normal range of resistivity.

7. A method for determining a hemodialysis patient's dry weight comprising the steps of:
periodically measuring the resistance of a body segment during hemodialysis;
comparing successive resistance measurements according to the equation $$\delta = R_0/R_t$$

wherein $\delta$ is the relative change in extracellular volume in the body segment, $R_0$ is the resistance in the body segment at the beginning of hemodialysis, and $R_t$ is the resistance in the body segment during hemodialysis at a time t; and identifying the hemodialysis patient's dry weight when a substantially constant resistivity is reached wherein $$\Delta\delta = (R_0/R_t - R_0/R_{t+1}) * 100\% \leq \text{about } 2\%$$

wherein $\Delta\delta$ is the relative change in the extracellular volume (ECV) during dialysis; $R_0$ is the resistance during dialysis at time 0; $R_t$ is the resistance during dialysis at time t; and $R_{t+1}$ is the resistance during dialysis at time t+1.

8. The method of claim 7, wherein identifying the hemodialysis patient's dry weight further comprises when resistivity $(\rho) \geq \rho N$, wherein $\rho N$ is a normal range of resistivity.

9. A device for monitoring hydration status in a hemodialysis patient comprising:
a digital signal processor;
an electrical output means being in electrical communication with the digital signal processor and being attachable to a body segment, the electrical output means being adapted to apply electrical current to the body segment;
an electrical input means being in electrical communication with the digital signal processor and being attachable to a body segment, the electrical input means being adapted to receive the current transmitted through the body segment and transmit the same to the digital signal processor; and
a microprocessor being in electrical communication with the digital signal processor;

wherein the microprocessor is adapted to determine a relative change in extracellular volume in the body segment based on a change in resistance in the body segment, and to plot said relative change as a function of time; and wherein the microprocessor determines the relative change in extracellular volume in the body segment according to the following equation:

$$\delta = R_0/R_t$$

wherein $\delta$ is the relative change in extracellular volume in the body segment, $R_0$ is the resistance in the body segment at the beginning of hemodialysis, and $R_t$ is the resistance in the body segment during hemodialysis at a time t.

10. A device for calculating cardiac output through bioimpedance measurements of a patient comprising:
a bioimpedance measurement unit;
a first electrical output means being in electrical communication with the bioimpedance analysis measurement unit and being attachable to an arm segment, the first electrical output means being adapted to apply electrical current to the arm segment;
a second electrical output means being in electrical communication with the bioimpedance analysis measurement unit and being attachable to a leg segment, the second electrical output means being adapted to apply electrical current to the leg segment;
a first electrical input means being in electrical communication with the bioimpedance analysis measurement unit and being attachable to an arm segment, the electrical input means being adapted to receive the current transmitted through the arm segment and transmit the same to the bioimpedance analysis measurement unit;
a second electrical input means being in electrical communication with the bioimpedance analysis measurement unit and being attachable to a leg segment, the electrical input means being adapted to receive the current transmitted through the leg segment and transmit the same to the bioimpedance analysis measurement unit;
a first pressure applying means for applying a maximum pressure to the arm segment, the first pressure applying means being in electrical communication with the bioimpedance analysis measurement unit;
a second pressure applying means for applying a maximum pressure to the leg segment, the second pressure applying means being in electrical communication with the bioimpedance analysis measurement unit; and
a means for selectively electronically connecting the bioimpedance analysis measurement unit between the first electrical input and output means and the second electrical input and output means;
wherein the bioimpedance analysis measurement unit is adapted to selectively measure stroke volume in the arm and leg segments by bioimpedance analysis.

* * * * *